(12) United States Patent  
Stout et al.

(10) Patent No.: US 8,748,379 B2  
(45) Date of Patent: Jun. 10, 2014

(54) RTEF-1 VARIANTS AND THE USE THEREOF FOR INHIBITION OF ANGIOGENESIS

(75) Inventors: J. Timothy Stout, Portland, OR (US); Trevor J. McFarland, Portland, OR (US); Binoy Appukuttan, Portland, OR (US)

(73) Assignee: Research Development Foundation, Carson City, NV (US)

( * ) Notice: Subject to any disclaimer, the term of this patent is extended or adjusted under 35 U.S.C. 154(b) by 1612 days.

(21) Appl. No.: 12/134,626

(22) Filed: Jun. 6, 2008

(65) Prior Publication Data

US 2009/0117119 A1  May 7, 2009

Related U.S. Application Data

(60) Provisional application No. 60/942,249, filed on Jun. 6, 2007.

(51) Int. Cl.
  *C07K 14/435* (2006.01)
  *A61K 38/00* (2006.01)
  *A61K 38/16* (2006.01)
  *A61K 38/17* (2006.01)

(52) U.S. Cl.
  USPC .......... 514/13.3; 514/1.1; 514/21.2; 530/300; 530/350

(58) Field of Classification Search
  None
  See application file for complete search history.

(56) References Cited

U.S. PATENT DOCUMENTS

| | | |
|---|---|---|
| 5,776,776 A | 7/1998 | Ordahl et al. |
| 5,994,136 A | 11/1999 | Naldini et al. |
| 6,013,516 A | 1/2000 | Verma et al. |
| 7,122,181 B2 | 10/2006 | Stout et al. |
| 7,183,388 B2 | 2/2007 | Denardo et al. |
| 2003/0008374 A1 | 1/2003 | Trono et al. |
| 2003/0082789 A1 | 5/2003 | Trono et al. |
| 2005/0175591 A1 | 8/2005 | Stout et al. |
| 2006/0223114 A1 | 10/2006 | Stemmer et al. |
| 2006/0234299 A1 | 10/2006 | Stemmer et al. |
| 2008/0138330 A1 | 6/2008 | Shie et al. |

FOREIGN PATENT DOCUMENTS

WO  WO 2005/034881  4/2005

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era, Trends in Biotech. 18(1):34-39.*
Benouchan et al. (2005). Anti-angiogenic strategies for cancer therapy (review). Intl. J. Oncology. 27:563-571.*
Shumizu et al. (2005). Antineovascular therapy, a novel antiangiogenic approach. Expert. Opin. Ther. Targets. 9(1):63-76.*
Neri et al. (2005). Tumour vascular targeting. Nature Reviews Cancer. 5:436-446.*
Eskens, F. (2004). Angiogenesis inhibitors in clinical development; where are we now and where are we going? British Journal of Cancer. 90:1-7.*
Sweeney et al. (2003). Resistance in the anti-angiogenic era: naysaying or a word of caution? Trends in Molecular Medicine. 9(1):24-29.*
Pettit et al. (1998). The development of site-specific drug-delivery systems for protein and peptide biopharmaceuticals. Trends in Biotechnology. 16: 343-349.*
Appukuttan et al., "Identification of novel alternatively spliced isoforms of RTEF-1 within human ocular vascular endothelial cells and murine retina," *Investigative Ophthalmology & Visual Science*, 48 (8): 3775-3782, 2007.
Donahue et al., "Retinal vascular endothelial growth factor (VEGF) mRNA expression is altered in relation to neovascularization in oxygen induced retinopathy," *Curr. Eye Res.*, 15 (2): 175-184, 1996.
Farrance et al., "The role of transcription enhancer factor-1 (TEF-1) related proteins in the formation of M-CAT binding complexes in muscle and non-muscle tissues," *J. Biol. Chem.*, 271 (14): 8266-8274, 1996.
Frigerio et al., "Analysis of 2166 clones from a human colorectal cancer cDNA library by partial sequencing," *Hum. Mol. Genet.*, 4 (1): 37-43, 1995.
Gragoudas et al., "Pegaptanib for neovascular age-related macular degeneration," *N. Engl. J. Med.*, 351 (27): 2805-2816, 2004.
Int. Search Report and Written Opinion, issued in Int. App. No. PCT/US2008/066058, dated Sep. 5, 2008.
Jiang et al., "Novel human TEF-1 isoforms exhibit altered DNA binding and functional properties," *Biochemistry*, 39 (12): 3505-3513, 2000.
Kanda et al., "Comparison of ICAM-1 and VCAM-1 expression in various human endothelial cell types and smooth muscle cells," *Endothelium.*, 6 (1): 33-44, 1998.

(Continued)

*Primary Examiner* — Christine J Saoud
*Assistant Examiner* — Jon M Lockard
(74) *Attorney, Agent, or Firm* — Parker Highlander PLLC

(57) ABSTRACT

Dominant negative (DN) variants of transcriptional enhancer factor 1-related (RTEF-1) are described. DN RTEF-1 polypeptides may be directly targeted to cells or delivered in nucleic acid expression vectors to alter cellular transcription. Methods for inhibiting VEGF production and thereby treating angiogenic disorders such as cancer are described. For example, in certain aspects, DN RTEF-1 may be used to treat angiogenic disorders of the eye such as age related macular degeneration (AMD).

42 Claims, 7 Drawing Sheets

(56) References Cited

OTHER PUBLICATIONS

Kaneko and DePamphilis, "Regulation of gene expression at the beginning of mammalian development and the TEAD family of transcription factors," *Dev. Genet.*, 22 (1): 43-55, 1998.

Kelleher and Vos, "Long-term episomal gene delivery in human lymphoid cells using human and avian adenoviral-assisted transfection," *Biotechniques*, 17 (6): 1110-1117, 1994.

Lashkari et al., "Vascular endothelial growth factor and hepatocyte growth factor levels are differentially elevated in patients with advanced retinopathy of prematurity," *Am. J. Pathol.*, 156 (4): 1337-1344, 2000.

Miller, "Vascular endothelial growth factor and ocular neovascularization," *Am. J. Pathol.*, 151 (1): 13-23, 1997.

Onda et al., "In vitro and in vivo cytotoxic activities of recombinant immunotoxin 8H9(Fv)-PE38 against breast cancer, osteosarcoma, and neuroblastoma," *Cancer Res.*, 64 (4): 1419-1424, 2004.

Pe-er et al., "Hypoxia-induced expression of vascular endothelial growth factor by retinal cells is a common factor in neovascularizing ocular diseases," *Lab. Invest.*, 72 (6): 638-645, 1995.

Pierce et al., "Regulation of vascular endothelial growth factor by oxygen in a model of retinopathy of prematurity," *Arch. Ophthalmol.*, 114 (10):1219-1228, 1996.

Rothbard et al., "Conjugation of arginine oligomers to cyclosporin A facilitates topical delivery and inhibition of inflammation," *Nat. Medicine*, 6 (11): 1253-1257, 2000.

Shie et al., "RTEF1, a novel transcriptional stimulator of endothelial growth factor in hypoxic endothelial cells," *J. of Biol. Chem.*, 279 (24): 25010-25016, 2004.

Silverman et al., "Differential E-selectin expression by iris versus retina microvascular endothelial cells cultured from the same individuals," *Microvasc. Res.*, 70 (1-2): 32-42, 2005.

Stewart et al., "Cloning of human RTEF-1, a transcriptional enhancer factor-1-related gene preferentially expressed in skeletal muscle: evidence for an ancient multigene family," *Genomics*, 37 (1): 68-76, 1996.

Vannay et al., "Association of genetic polymorphisms of vascular endothelial growth factor and risk for proliferative retinopathy of prematurity," *Pediatr. Res.*, 57 (3): 396-398, 2005.

Von Minckwitz et al., "Phase I clinical study of the recombinant antibody toxin scFv(FRP5)-ETA specific for the ErbB2/HER2 receptor in patients with advanced solid malignomas," *Breast Cancer Res.*, 7 (5): R616-626, 2005.

Winthrop et al., "Selection and characterization of anti-MUC-1 scFvs intended for targeted therapy," *Clin. Cancer Res.*, 9 (10 pt. 2): 3845s-3853s, 2003.

Wright et al., "Guanidinium rich peptide transporters and drug delivery," *Curr. Protein Pept. Sci.*, 4 (2): 105-124, 2003.

Yasunami et al., "A novel family of TEA domain-containing transcription factors with distinct spatiotemporal expression patterns," *Biochem. Biohpys. Res. Commun.*, 228 (2): 364-370, 1996.

Yockey et al., "cDNA cloning and characterization of murine transcriptional enhancer factor-1-related protein 1, a transcription factor that binds to the M-CAT motif," *J. of Biol. Chem.*, 271 (7): 3727-3736, 1996.

Young et al., "Histopathology and vascular endothelial growth factor in untreated and diode laser-treated retinopathy of prematurity," *J Aapos.*, 1 (2): 105-110, 1997.

Zuzarte et al., "Tumor cell splice variants of the transcription factor TEF-1 induced by SV40 T-antigen transformation," *Biochim. Biophys. Acta.*, 1517 (1): 82-90, 2000.

\* cited by examiner

FIG. 1A-B

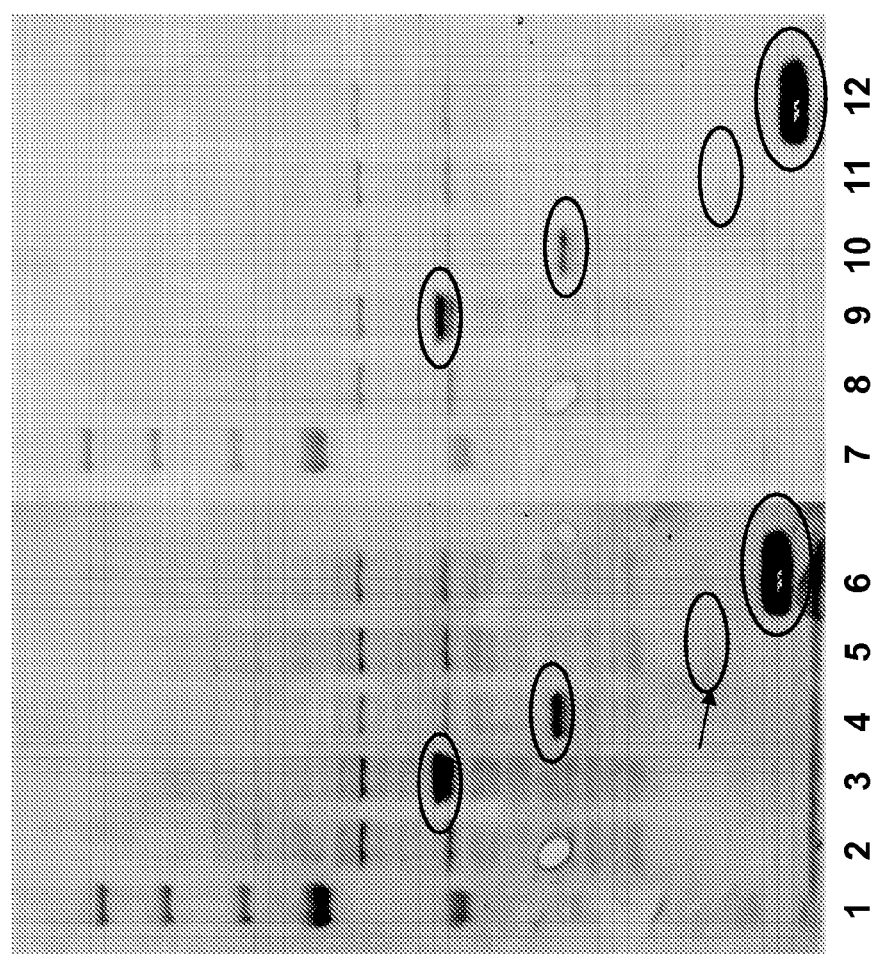
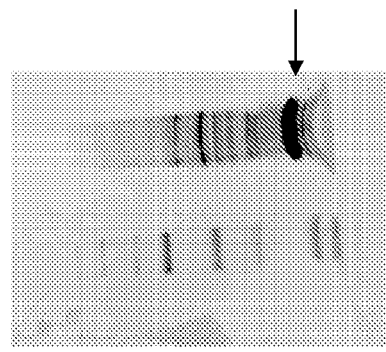
A
hTEAD1  MERMSDSA----------------DKPIDN- SEQ ID NO:16
hTEAD2  MGEPRAGAALDDGSGWTGSEEGSEEGTGGSEGAGGDGGP SEQ ID NO:17
hTEAD3  MASNSWNASSSPGEAREDGPEG------LDKGLDN- SEQ ID NO:18
RTEF-1  MEGTAGTITSNEWSSPTS-PEGSTASGGSQALDKPIDN- SEQ ID NO:19
        -*************************************
FIG. 5A-C

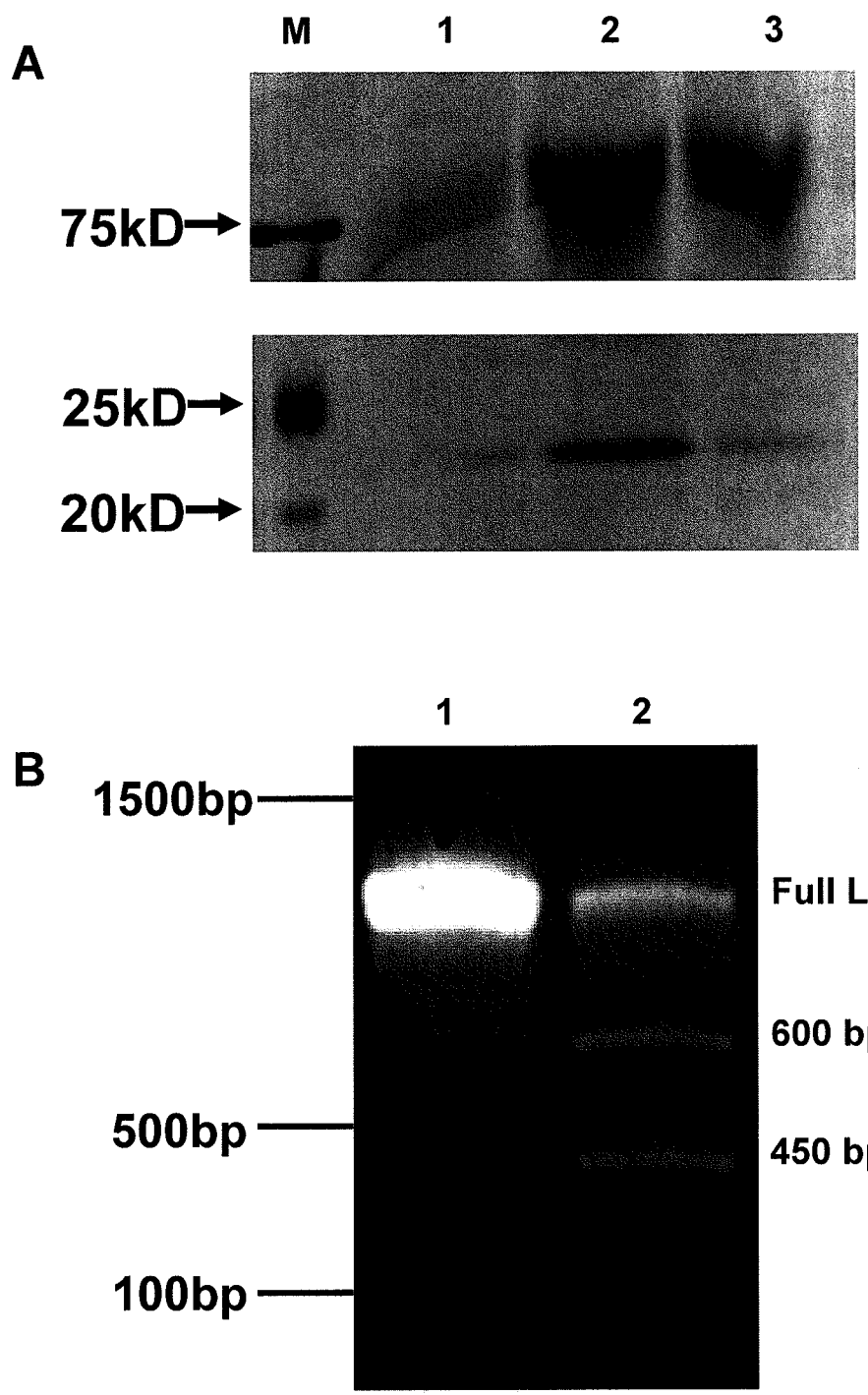
FIG. 6A-B

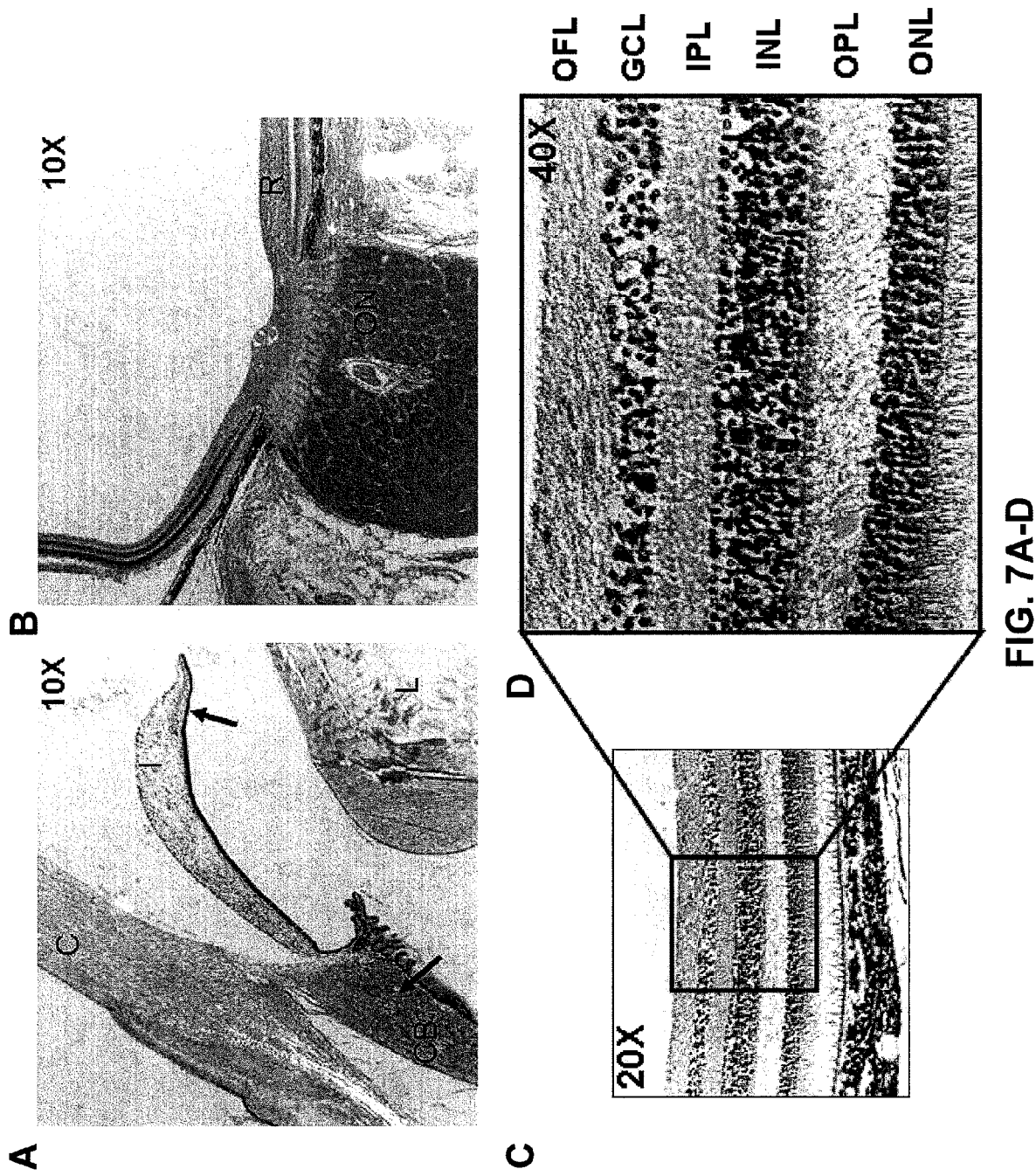
FIG. 7A-D

SEQUENCE LISTING

```
<160> NUMBER OF SEQ ID NOS: 23

<210> SEQ ID NO 1
<211> LENGTH: 436
<212> TYPE: PRT
<213> ORGANISM: Homo sapiens

<400> SEQUENCE: 1

Leu Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn Asp Gly Glu Gly Val Trp Ser Pro Asp Ile Glu
        35                  40                  45

Gln Ser Phe Gln Glu Ala Leu Ala Ile Tyr Pro Pro Cys Gly Arg Arg
    50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Arg Thr Arg Lys
                85                  90                  95

Gln Val Ser Ser His Ile Gln Val Leu Ala Arg Arg Lys Ala Arg Glu
            100                 105                 110

Ile Gln Ala Lys Leu Lys Asp Gln Ala Ala Lys Asp Lys Ala Leu Gln
        115                 120                 125

Ser Met Ala Ala Met Ser Ser Ala Gln Ile Ile Ser Ala Thr Ala Phe
    130                 135                 140

His Ser Ser Met Arg Leu Ala Arg Gly Pro Gly Arg Pro Ala Val Ser
145                 150                 155                 160

Gly Phe Trp Gln Gly Ala Leu Pro Gly Gln Ala Glu Thr Ser His Asp
                165                 170                 175
```

Val Lys Pro Phe Ser Gln Gln Thr Tyr Ala Val Gln Pro Pro Leu Pro
            180                 185                 190

Leu Pro Gly Phe Glu Ser Pro Ala Gly Pro Ala Pro Ser Pro Ser Ala
        195                 200                 205

Pro Pro Ala Pro Pro Trp Gln Gly Arg Arg Gly Ser Ser Lys Leu
    210                 215                 220

Trp Met Leu Glu Phe Ser Ala Phe Leu Glu Gln Gln Asp Pro Asp
225                 230                 235                 240

Thr Tyr Asn Lys His Leu Phe Val His Ile Gly Gln Ser Ser Pro Ser
                245                 250                 255

Tyr Leu Arg Pro Tyr Leu Glu Ala Val Asp Ile Arg Gln Ile Tyr Asp
            260                 265                 270

Lys Phe Pro Glu Lys Lys Gly Gly Leu Lys Asp Leu Phe Glu Arg Gly
        275                 280                 285

Pro Ser Asn Ala Phe Phe Leu Val Lys Phe Trp Ala Asp Leu Asn Thr
    290                 295                 300

Asn Leu Leu Glu Glu Asp Gly Ser Ser Phe Tyr Gly Val Ser Ser
305                 310                 315                 320

Gln Tyr Glu Ser Pro Glu Asn Met Ile Ile Thr Cys Ser Thr Lys Val
                325                 330                 335

Cys Ser Phe Gly Lys Gln Val Val Glu Lys Val Glu Thr Glu Tyr Ala
            340                 345                 350

Arg Tyr Glu Asn Gly His Tyr Ser Tyr Arg Ile His Arg Ser Pro Leu
        355                 360                 365

Cys Glu Tyr Met Ile Asn Phe Ile His Lys Leu Lys His Leu Pro Glu
370                 375                 380

Lys Tyr Met Met Asn Ser Val Leu Glu Asn Phe Thr Ile Leu Gln Val
385                 390                 395                 400

Val Thr Asn Arg Asp Thr Gln Glu Thr Leu Leu Cys Ile Ala Tyr Val
                405                 410                 415

Phe Glu Val Ser Ala Ser Glu His Gly Ala Gln His His Ile Tyr Arg
            420                 425                 430

Leu Val Lys Glu
        435

<210> SEQ ID NO 2
<211> LENGTH: 311
<212> TYPE: PRT
<213> ORGANISM: Homo sapiens

<400> SEQUENCE: 2

Leu Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn Asp Gly Glu Gly Val Trp Ser Pro Asp Ile Glu
        35                  40                  45

Gln Ser Phe Gln Glu Ala Leu Ala Ile Tyr Pro Pro Cys Gly Arg Arg
    50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Arg Thr Arg Lys
                85                  90                  95

Gln Val Ser Ser His Ile Gln Val Leu Ala Arg Arg Lys Ala Arg Glu
            100                 105                 110

```
Ile Gln Ala Lys Leu Lys Tyr Asn Lys His Leu Phe Val His Ile Gly
            115                 120                 125

Gln Ser Ser Pro Ser Tyr Leu Arg Pro Tyr Leu Glu Ala Val Asp Ile
    130                 135                 140

Arg Gln Ile Tyr Asp Lys Phe Pro Glu Lys Lys Gly Leu Lys Asp
145                 150                 155                 160

Leu Phe Glu Arg Gly Pro Ser Asn Ala Phe Phe Leu Val Lys Phe Trp
                165                 170                 175

Ala Asp Leu Asn Thr Asn Ile Glu Asp Glu Gly Ser Ser Phe Tyr Gly
            180                 185                 190

Val Ser Ser Gln Tyr Glu Ser Pro Glu Asn Met Ile Ile Thr Cys Ser
    195                 200                 205

Thr Lys Val Cys Ser Phe Gly Lys Gln Val Val Glu Lys Val Glu Thr
210                 215                 220

Glu Tyr Ala Arg Tyr Glu Asn Gly His Tyr Ser Tyr Arg Ile His Arg
225                 230                 235                 240

Ser Pro Leu Cys Glu Tyr Met Ile Asn Phe Ile His Lys Leu Lys His
                245                 250                 255

Leu Pro Glu Lys Tyr Met Met Asn Ser Val Leu Glu Asn Phe Thr Ile
            260                 265                 270

Leu Gln Val Val Thr Asn Arg Asp Thr Gln Glu Thr Leu Leu Cys Ile
    275                 280                 285

Ala Tyr Val Phe Glu Val Ser Ala Ser Glu His Gly Ala Gln His His
290                 295                 300

Ile Tyr Arg Leu Val Lys Glu
305                 310

<210> SEQ ID NO 3
<211> LENGTH: 216
<212> TYPE: PRT
<213> ORGANISM: Homo sapiens

<400> SEQUENCE: 3

Leu Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
                20                  25                  30

Lys Pro Ile Asp Asn Asp Gly Glu Gly Val Trp Ser Pro Asp Ile Glu
            35                  40                  45

Gln Ser Phe Gln Glu Ala Leu Ala Ile Tyr Pro Pro Cys Gly Arg Arg
    50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Ser Ser Phe Tyr
                85                  90                  95

Gly Val Ser Ser Gln Tyr Glu Ser Pro Glu Asn Met Ile Ile Thr Cys
                100                 105                 110

Ser Thr Lys Val Cys Ser Phe Gly Lys Gln Val Val Glu Lys Val Glu
            115                 120                 125

Thr Glu Tyr Ala Arg Tyr Glu Asn Gly His Tyr Ser Tyr Arg Ile His
        130                 135                 140

Arg Ser Pro Leu Cys Glu Tyr Met Ile Asn Phe Ile His Lys Leu Lys
145                 150                 155                 160

His Leu Pro Glu Lys Tyr Met Met Asn Ser Val Leu Glu Asn Phe Thr
                165                 170                 175
```

```
Ile Leu Gln Val Val Thr Asn Arg Asp Thr Gln Glu Thr Leu Leu Cys
                180                 185                 190

Ile Ala Tyr Val Phe Glu Val Ser Ala Ser Glu His Gly Ala Gln His
            195                 200                 205

His Ile Tyr Arg Leu Val Lys Glu
    210                 215

<210> SEQ ID NO 4
<211> LENGTH: 148
<212> TYPE: PRT
<213> ORGANISM: Homo sapiens

<400> SEQUENCE: 4

Leu Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn Asp Gly Glu Gly Val Trp Ser Pro Asp Ile Glu
        35                  40                  45

Gln Ser Phe Gln Glu Ala Leu Ala Ile Tyr Pro Pro Cys Gly Arg Arg
    50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Arg Thr Arg Lys
                85                  90                  95

Gln Val Ser Ser His Ile Gln Val Leu Ala Arg Arg Lys Ala Arg Glu
            100                 105                 110

Ile Gln Ala Lys Leu Lys Phe Trp Gln Gly Ala Leu Pro Gly Gln Ala
        115                 120                 125

Glu Thr Ser His Asp Val Lys Pro Phe Ser Gln His Ile Tyr Arg
    130                 135                 140

Leu Val Lys Glu
145

<210> SEQ ID NO 5
<211> LENGTH: 76
<212> TYPE: PRT
<213> ORGANISM: Homo sapiens

<400> SEQUENCE: 5

Leu Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn Asp Ala Glu Gly Val Trp Ser Pro Asp Ile Glu
        35                  40                  45

Gln Ser Phe Gln Glu Ala Leu Ala Ile Tyr Pro Pro Cys Gly Arg Arg
    50                  55                  60

Lys Ile Ile Leu Ser Asp Glu Gly Lys Met Tyr Gly
65                  70                  75

<210> SEQ ID NO 6
<211> LENGTH: 21
<212> TYPE: PRT
<213> ORGANISM: Homo sapiens

<400> SEQUENCE: 6

Arg Asn Glu Leu Ile Ala Arg Tyr Ile Lys Leu Arg Thr Gly Lys Thr
1               5                   10                  15
```

Arg Thr Arg Lys Gln
            20

<210> SEQ ID NO 7
<211> LENGTH: 21
<212> TYPE: PRT
<213> ORGANISM: Homo sapiens

<400> SEQUENCE: 7

Val Ser Ser His Ile Gln Val Leu Ala Arg Arg Lys Ala Arg Glu Ile
1               5                   10                  15

Gln Ala Lys Leu Lys
            20

<210> SEQ ID NO 8
<211> LENGTH: 43
<212> TYPE: PRT
<213> ORGANISM: Homo sapiens

<400> SEQUENCE: 8

Asp Gln Ala Ala Lys Asp Lys Ala Leu Gln Ser Met Ala Ala Met Ser
1               5                   10                  15

Ser Ala Gln Ile Ile Ser Ala Thr Ala Phe His Ser Ser Met Ala Leu
            20                  25                  30

Ala Arg Gly Pro Gly Arg Pro Ala Val Ser Gly
            35                  40

<210> SEQ ID NO 9
<211> LENGTH: 15
<212> TYPE: PRT
<213> ORGANISM: Homo sapiens

<400> SEQUENCE: 9

Phe Trp Gln Gly Ala Leu Pro Gly Gln Ala Gly Thr Ser His Asp
1               5                   10                  15

<210> SEQ ID NO 10
<211> LENGTH: 19
<212> TYPE: PRT
<213> ORGANISM: Homo sapiens

<400> SEQUENCE: 10

Val Lys Pro Phe Ser Gln Gln Thr Tyr Ala Val Gln Pro Pro Leu Pro
1               5                   10                  15

Leu Pro Gly

<210> SEQ ID NO 11
<211> LENGTH: 46
<212> TYPE: PRT
<213> ORGANISM: Homo sapiens

<400> SEQUENCE: 11

Phe Glu Ser Pro Ala Gly Pro Ala Pro Ser Pro Ser Ala Pro Pro Ala
1               5                   10                  15

Pro Pro Trp Gln Gly Arg Ser Val Ala Ser Ser Lys Leu Trp Met Leu
            20                  25                  30

Glu Phe Ser Ala Phe Leu Glu Gln Gln Gln Asp Pro Asp Thr
            35                  40                  45

<210> SEQ ID NO 12
<211> LENGTH: 58
<212> TYPE: PRT

<213> ORGANISM: Homo sapiens

<400> SEQUENCE: 12

Tyr Asn Lys His Leu Phe Val His Ile Gly Gln Ser Ser Pro Ser Tyr
1               5                   10                  15
Ser Asp Pro Tyr Leu Glu Ala Val Asp Ile Arg Gln Ile Tyr Asp Lys
            20                  25                  30
Phe Pro Glu Lys Lys Gly Gly Leu Lys Asp Leu Phe Glu Arg Gly Pro
        35                  40                  45
Ser Asn Ala Phe Phe Leu Val Lys Phe Trp
    50                  55

<210> SEQ ID NO 13
<211> LENGTH: 47
<212> TYPE: PRT
<213> ORGANISM: Homo sapiens

<400> SEQUENCE: 13

Ala Asp Leu Asn Thr Asn Ile Glu Asp Glu Gly Ser Ser Phe Tyr Gly
1               5                   10                  15
Val Ser Ser Gln Tyr Glu Ser Pro Glu Asn Met Ile Ile Thr Cys Ser
            20                  25                  30
Thr Lys Val Cys Ser Phe Gly Lys Gln Val Val Glu Lys Val Glu
        35                  40                  45

<210> SEQ ID NO 14
<211> LENGTH: 51
<212> TYPE: PRT
<213> ORGANISM: Homo sapiens

<400> SEQUENCE: 14

Thr Glu Tyr Ala Arg Tyr Glu Asn Gly His Tyr Ser Tyr Arg Ile His
1               5                   10                  15
Arg Ser Pro Leu Cys Glu Tyr Met Ile Asn Phe Ile His Lys Leu Lys
            20                  25                  30
His Leu Pro Glu Lys Tyr Met Met Asn Ser Val Leu Glu Asn Phe Thr
        35                  40                  45
Ile Leu Gln
    50

<210> SEQ ID NO 15
<211> LENGTH: 37
<212> TYPE: PRT
<213> ORGANISM: Homo sapiens

<400> SEQUENCE: 15

Val Val Thr Asn Arg Asp Thr Gln Glu Thr Leu Leu Cys Ile Ala Tyr
1               5                   10                  15
Val Phe Glu Val Ser Ala Ser Glu His Gly Ala Gln His His Ile Tyr
            20                  25                  30
Arg Leu Val Lys Glu
        35

<210> SEQ ID NO 16
<211> LENGTH: 14
<212> TYPE: PRT
<213> ORGANISM: Homo sapiens

<400> SEQUENCE: 16

Met Glu Arg Met Ser Asp Ser Ala Asp Lys Pro Ile Asp Asn
1               5                   10

```
<210> SEQ ID NO 17
<211> LENGTH: 39
<212> TYPE: PRT
<213> ORGANISM: Homo sapiens

<400> SEQUENCE: 17

Met Gly Glu Pro Arg Ala Gly Ala Ala Leu Asp Asp Gly Ser Gly Trp
1               5                   10                  15

Thr Gly Ser Glu Glu Gly Ser Glu Glu Gly Thr Gly Ser Glu Gly
            20                  25                  30

Ala Gly Gly Asp Gly Gly Pro
        35

<210> SEQ ID NO 18
<211> LENGTH: 29
<212> TYPE: PRT
<213> ORGANISM: Homo sapiens

<400> SEQUENCE: 18

Met Ala Ser Asn Ser Trp Asn Ala Ser Ser Pro Gly Glu Ala Arg
1               5                   10                  15

Glu Asp Gly Pro Glu Gly Leu Asp Lys Gly Leu Asp Asn
            20                  25

<210> SEQ ID NO 19
<211> LENGTH: 37
<212> TYPE: PRT
<213> ORGANISM: Homo sapiens

<400> SEQUENCE: 19

Met Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn
        35

<210> SEQ ID NO 20
<211> LENGTH: 19
<212> TYPE: DNA
<213> ORGANISM: Artificial
<220> FEATURE:
<223> OTHER INFORMATION: Artificial primer

<400> SEQUENCE: 20
ttggagggca cggccggca                                                19

<210> SEQ ID NO 21
<211> LENGTH: 21
<212> TYPE: DNA
<213> ORGANISM: Artificial
<220> FEATURE:
<223> OTHER INFORMATION: Artificial primer

<400> SEQUENCE: 21
tcattctttc accagcctgt a                                             21

<210> SEQ ID NO 22
<211> LENGTH: 20
<212> TYPE: PRT
<213> ORGANISM: Homo sapiens

<400> SEQUENCE: 22
```

```
Met Tyr Arg Met Gln Leu Leu Ser Cys Ile Ala Leu Ser Leu Ala Leu
1               5                   10                  15

Val Thr Asn Ser
            20

<210> SEQ ID NO 23
<211> LENGTH: 10
<212> TYPE: PRT
<213> ORGANISM: Artificial
<220> FEATURE:
<223> OTHER INFORMATION: Artificial primer

<400> SEQUENCE: 23

Arg Met Arg Arg Met Arg Arg Met Arg Arg
1               5                   10
```

RTEF-1 VARIANTS AND THE USE THEREOF FOR INHIBITION OF ANGIOGENESIS

This application claims priority to U.S. Application No. 60/942,249 filed on Jun. 6, 2007, the entire disclosure of which is specifically incorporated herein by reference in its entirety without disclaimer.

BACKGROUND OF THE INVENTION

1. Field of the Invention

The invention concerns the fields of molecular biology and specifically concerns processes involving blood vessel formation (angiogenesis).

2. Description of Related Art

Transcriptional enhancer factor 1-related (RTEF-1) gene is a member of the TEA DNA binding domain gene family. The TEA DNA binding domain gene family is highly conserved from *Aspergillus nidulans*, yeast, *Drosophila*, mice to human. The TEA DNA binding family of proteins can be involved in both activation and repression of different genes and their particular function can be modified by association with other proteins (Kaneko & DePamphilis, 1998). Expression of specific members of these genes has been identified in various mammalian tissues, including heart, skeletal muscle, pancreas, placenta, brain and lung (Stewart et al., 1996; Yasunami et al., 1996; Farrance et al., 1996). Isoforms arising from alternative splicing of mRNA from a single gene, for transcriptional enhancer factor-1 (TEF-1) have been identified within a single tissue such as the pancreas (Zuzarte et al., 2000; Jiang et al., 2000). The expression profile of these genes within the mammalian eye has not been reported.

Transcripts of the RTEF-1 gene were first identified in chicken tissue and demonstrated to be enriched in cardiac and skeletal muscle (Farrance et al., 1996). The chicken RTEF-1 binds to the myocyte-specific CAT (M-CAT) cis DNA elements and regulates expression of muscle specific genes, and requires muscle specific cofactors for full transcriptional activation. Random screening of 2166 human colorectal cancer cDNA library identified a partial cDNA RTEF-1 sequence which lead to the isolation of a full length human homolog of the avian RTEF-1 from a heart cDNA library (Stewart et al., 1996; Frigerio et al., 1995). Northern blot analysis of human tissue indicated highest levels of expression in skeletal muscle and pancreas, with lower levels in heart, kidney and placenta, whereas message was not detected in liver, lung or brain (Stewart et al., 1996). Northern blot analysis of the mouse homolog of RTEF-1 indicates a different tissue expression pattern when compared to human. Adult mouse lung tissue expressed the highest level, with very low levels in kidney, heart and skeletal muscle and undetectable amounts in liver, thymus, spleen and brain, whereas RTEF-1 message was abundant in mouse embryonic skeletal muscle (Yockey et al., 1996). An alternatively spliced mouse isoform of RTEF-1 that lacks exon 5 when compare to the full length gene has been identified in mouse skeletal muscle cells (Yockey et al., 1996).

Vascular endothelial growth factor (VEGF) is one pro-angiogenic factor that is known to be up regulated in retinal tissue under hypoxic conditions (Young et al., 1997; Pierce et al., 1996; Donahue et al., 1996; Pe'er et al., 1995). Recently the full length RTEF-1 protein has been identified to not only bind to the VEGF promoter but also to up-regulate the expression of VEGF, for instance under hypoxic conditions in bovine aortic endothelial cells (BAEC) (Shie et al., 2004). Microarray analysis revealed that RTEF-1 expression was up-regulated by 3-fold in BAEC under hypoxic conditions. Surprisingly, RTEF-1 mediated VEGF gene activation via interaction with Sp1 elements within the VEGF promoter and not M-CAT motifs. In addition RTEF mediated expression of VEGF is achieved independently of the hypoxia-inducible factor (HIF-1) and hypoxia responsive element (HRE) pathway of activation (Shie et al., 2004).

VEGF over-expression has been implicated in a variety of angiogenic disorders such as tumor angiogenesis and aberrant neovascularization. For example, it is well established that VEGF plays an important role in the development and severity of retinopathy of prematurity (ROP) and other ocular neovascular diseases (Lashkari et al., 2000; Miller, 1997; Vannay et al., 2005; Young et al., 1997). Given the prominent role of VEGF in such disorders a number of therapeutic strategies for inhibiting VEGF activity have been developed. However, current VEGF blockade therapies typically involve inhibiting the interaction of extra cellular VEGF with cognate cell surface receptors. Thus, there is a need for alternative strategies for VEGF blockade such as method for inhibiting VEGF production.

SUMMARY OF THE INVENTION

In a first embodiment, the invention provides an isolated dominant negative (DN) RTEF-1 polypeptide comprising an RTEF-1 amino acid sequence with one or more internal deletions. As used herein the term dominant negative means that the RTEF-1 variant suppresses or reduces the activity of an intact RTEF-1 polypeptide as exemplified by SEQ ID NO:1. For example, in certain aspects, a DN RTEF-1 variant may be defined as a polypeptide that when expressed in a cell inhibits or reduces VEGF promoter activity. Furthermore, in some cases, a DN RTEF-1 may be defined as a polypeptide that reduces or inhibits hypoxia induced or RTEF-1 (e.g., SEQ ID NO:1, SEQ ID NO:2 or SEQ ID NO:4) induced VEGF promoter activity. In certain aspects, a RTEF-1 amino acid sequence may be a mammalian RTEF-1 amino acid sequence, preferably a human RTEF-1 amino acid sequence.

Thus, in certain aspects there is provided a DN RTEF-1 polypeptide comprising one or more internal amino acid deletions. For example, in certain cases a DN RTEF-1 may comprise a deletion of amino acids encoded by exons 3, 4, 5, 6, 7, 8, 9 or 10. For example, in certain specific embodiments, a DN RTEF-1 may comprise a deletion of all of the amino acids sequence encoded by exons 4, 5, 6, 7, 8 and/or 9. Furthermore, in certain specific cases, a DN RTEF-1 may comprise a partial deletion of amino acids from exon 3 and/or exon 10, such as a deletion of about the last 5 amino acids encoded by exon 3 or deletion of about the first 11 amino acids encoded by exon 10. Furthermore it will be understood by the skilled artisan that a DN RTEF-1 may comprise amino acid substitutions relative to a wild type RTEF-1 sequence, such as human RTEF-1 sequence. Thus, in certain cases, a DN RTEF-1 may be defined as a RTEF-1 polypeptide comprising one or more internal amino acid deletions wherein the DN RTEF-1 is about or at least about 70, 75, 80, 85, 90, 95, 98 or 99 percent identical to a wild type RTEF-1 sequence (e.g., SEQ ID NO:1, SEQ ID NO:2 or SEQ ID NO:4) over the undeleted amino acid region. In some very specific aspects a RTEF-1 dominant negative polypeptide may comprise a RTEF-1 amino acid sequence is about or at least about 70, 75, 80, 85, 90, 95, 98 or 99 percent identical to SEQ ID NO:3 (the amino acid sequence encoded by the 651 bp cDNA). In some very specific aspects the DN RTEF-1 polypeptide may comprise the sequence given by SEQ ID NO:3. Further embodiments of DN RTEF-1 polypeptides contemplated by the invention are provided in the detailed description of the embodiments.

In some further aspects a DN RTEF-1 polypeptide may comprise a cell internalization moiety. In some cases a cell internalization moiety may be associated with or conjugated to a DN RTEF-1 polypeptide. For example, a DN RTEF-1 may be provided in complex with a liposomal vesicles thereby enabling the polypeptide to traverse the cell membrane. Furthermore, in some specific embodiments a cell internalization moiety may be a peptide, a polypeptide, an aptamer or an avimer (see for example U.S. Applns. 20060234299 and 20060223114) sequence. For example, a cell internalization moiety may comprise amino acids from the HIV tat, HSV-1 tegument protein VP22, or *Drosophila* antennopedia. In certain further aspects, a cell internalization moiety may be a engineered internalization moiety such as the poly-Arginine, Methionine and Glycine peptides described by Wright et al. (2003) and Rothbard et al. (2000). For example, a cell internalization moiety may be the RMR-RMRRMRR (SEQ ID NO:23) exemplified herein. Thus, in some cases a polypeptide cell internalization moiety and a DN RTEF-1 polypeptide may comprise a fusion protein.

Thus, in certain cases, DN RTEF-1 fusion proteins are provided comprising a cell internalization moiety and a DN RTEF-1 sequence. The skilled artisan with understand that such fusion proteins may additionally comprises a one or more amino acid sequences separating the cell internalizing moiety and the DN RTEF-1 polypeptide sequence. For example, in some cases a linker sequence may separate these two domains. For example, a linker sequences may comprise a "flexible" amino acids with a large number or degrees of conformational freedom such as a poly glycine linker. In some cases, a linker sequence may comprising a proteinase cleavage site. For instance, in certain aspects, a linker sequence may comprising a cleavage site that is recognized and cleaved by an intracellular proteinase thereby releasing a DN RTEF-1 sequence from the cell internalization sequence once the fusion protein has been internalized.

In further aspects of the invention a cell internalization moiety may be further defined as a cell targeting moiety, that is a moiety that binds to or is internalized by only a selected population of cells such as cells expressing a particular cellular receptor. Such a cell targeting may, for example, comprise an antibody, a growth factor, a hormone, a cytokine, an aptamer or an avimer that binds to a cell surface protein. As used herein the term antibody may refer to an IgA, IgM, IgE, IgG, a Fab, a F(ab')2, single chain antibody or paratope peptide. In certain cases, a cell targeting moiety of the invention may target a particular type of cells such as a retinal, endothelial, iris or neuronal cell. In still further aspects a cell targeting moiety of the invention may be defined as cancer cell binding moiety. For example, in some very specific cases a cell targeting moiety of the invention may target a cancer cell associated antigen such a gp240 or Her-2/neu.

In still further aspects of the invention a DN RTEF-1 polypeptide may comprise additional amino acid sequences such as a cell trafficking signals (e.g., cell secretion signal, a nuclear localization signal or a nuclear export signal) or a reporter polypeptides such as an enzyme or a fluorescence protein. In a preferred aspect for example, a DN RTEF-1 polypeptide comprises a cellular secretion signal. For example, as exemplified herein a DN RTEF-1 polypeptide may comprise a secretion sequence from a human gene such as the IL-2 secretion signal sequence (MYRMQLLSCIAL-SLALVTNS, SEQ ID NO:22). Thus, in certain cases, a DN RTEF-1 polypeptide may comprise a cell internalization moiety and cell secretion signal, thereby allowing the polypeptide to be secreted by one cells and internalized into a surrounding a cell.

In a further embodiment of the invention there is provided an isolated nucleic acid sequence comprising sequence encoding a DN RTEF-1 polypeptide as described supra. Thus, a nucleic acid sequence encoding any of the DN RTEF-1 polypeptides or polypeptide fusion proteins described herein are also included as part of the instant invention. The skilled artisan will understand that a variety of nucleic acid sequence may be used to encode identical polypeptides in view of the degeneracy of genetic code. In certain cases for example the codon encoding any particular amino acid may be altered to improve cellular expression or to reduce the chance that a nucleic acid may recombine at a genomic RTEF-1 locus.

In preferred aspects, a nucleic acid sequence encoding a DN RTEF-1 polypeptide is comprised in an expression cassette. As used herein the term "expression cassette" means that additional nucleic acids sequences are included that enable expression of DN RTEF-1 in a cell, or more particularly in a eukaryotic cell. Such additional sequences may, for examples, comprise a promoter, an enhancer, intron sequences (e.g., before after or with in the DN RTEF-1 coding region) or a polyadenylation signal sequence. The skilled artisan will recognize that sequences included in an expression cassette may be used to alter the expression characteristics of a DN RTEF-1. For instance, cell type specific, conditional or inducible promoter sequences may be used to restrict DN RTEF-1 to selected cell types or growth conditions. For example, in certain cases a hypoxia inducible promoter may be used in RTEF-1 expression cassettes of the invention. Furthermore, in some instances promoters with enhanced activity in cancer cells or cells of the eye may be employed. Furthermore, it is contemplated that certain alterations may be made to the RTEF-1 polypeptide sequence in order to enhance expression from an expression cassette for example, as exemplified herein, the initiation codon of a DN RTEF-1 may be changes to ATG to facilitate efficient translation.

In still further aspects of the invention a DN RTEF-1 coding sequence may be comprised in an expression vector such as a viral expression vector. Viral expression vectors for use according to the invention include but are not limited to adenovirus, adeno-associated virus, herpes virus, SV-40, retrovirus and vaccinia virus vector systems. In certain preferred aspects, a retroviral vector may be further defined as a lentiviral vector. In some cases such lentiviral vectors may be self-inactivating (SIN) lentiviral vector such as those described in U.S. Applns. 20030008374 and 20030082789 incorporated herein by reference.

In still further embodiments, the present invention concerns methods for reducing or inhibiting RTEF-1 dependent transcriptional activity. As used herein the term RTEF-1 dependent transcriptional activity refers to transcription that is mediated or enhanced by expression of an full length or fully active RTEF-1 polypeptide, as exemplified by SEQ ID NO:1, SEQ ID NO:2 or SEQ ID NO:4. Thus, in some respects, the invention provides methods for inhibiting or reducing VEGF promoter activity (and thereby VEGF expression) comprising expressing a DN RTEF-1 polypeptide in a cell. Thus, in a specific embodiment, there is provided a method for treating a patient with an angiogenic disorder comprising administering to the patient an effective amount of a therapeutic composition comprising a RTEF-1 dominant negative polypeptide or a nucleic acid expression vector encoding a RTEF-1 dominant negative polypeptide as described supra. In preferred aspects, methods described herein may used to treat a human patient.

As used herein the term angiogenic disorder refers to disorders involving a undesirable vascularization such as ocular neovascularization, arterio-venous malformations, coronary restenosis, peripheral vessel restenosis, glomerulonephritis, rheumatoid arthritis or cancer (e.g., tumor vascularization). Thus, in certain cases, methods of the invention may be used to treat ocular disorders such as macular degeneration (e.g., age-related macular degeneration (AMD)), corneal graft rejection, corneal neovascularization, retinopathy of prematurity (ROP) and diabetic retinopathy. For example, methods of the invention may be used in the treatment of wet or dry AMD. Thus, in certain cases, methods of the invention may be used to treat a number AMD associated ocular lesions such as predominantly classic, minimally classic, and occult with no classic lesions (Gragoudas et al., 2004).

The skilled artisan will understand that additional antiangiogenic therapies may be used in combination or in conjunction with methods of the invention. Such additional therapies may be administered before, after or essentially simultaneously with the methods descried herein. For example additional antiangiogenic therapies may antagonize the VEGF and/or FGF signaling pathway. Thus, in some cases and additional therapy may comprise administration an antibody that binds to VEGF, a VEGF receptor, FGF or an FGF receptor. In certain specific aspects, methods and compositions of the invention may be used in conjunction with AVASTIN® (bevacizumab), LUCENTIS® (ranibizumab), MACUGEN® (pegatanib sodium) or an anti-inflammatory drug. Thus, in certain specific cases there is provided a therapeutic composition comprising a DN-RTEF-1 composition and bevacizumab or pegatanib sodium in a pharmaceutically acceptable carrier. In still further aspects a gene that regulates angiogenesis may be delivered in conjunction with the methods of the invention. For example, in some aspects, a gene that regulates angiogenesis may be a tissue inhibitor of metalloproteinase, endostatin, angiostatin, endostatin XVIII, endostatin XV, kringle 1-5, PEX, the C-terminal hemopexin domain of matrix metalloproteinase-2, the kringle 5 domain of human plasminogen, a fusion protein of endostatin and angiostatin, a fusion protein of endostatin and the kringle 5 domain of human plasminogen, the monokine-induced by interferon-gamma (Mig), the interferon-alpha inducible protein 10 (IP10), a fusion protein of Mig and IP10, soluble FLT-1 (fms-like tyrosine kinase 1 receptor), and kinase insert domain receptor (KDR) gene. In certain specific aspects, such an angiogenic regulator gene may be delivered in a viral vector such as the lentiviral vectors described in U.S. Pat. No. 7,122,181, incorporated herein by reference.

As described above, in certain aspects, the invention provides methods for treating cancer. Thus, in certain cases, described methods may be used to limit or reduce blood flow to a tumor thereby reducing tumor growth or metastasis. In certain cases, the methods herein may be used to inhibit or treat metastatic cancers. A variety of cancer types may be treated with methods of the invention, for example a cancer for treatment may be a bladder, blood, bone, bone marrow, brain, breast, colon, esophagus, eye, gastrointestinal, gum, head, kidney, liver, lung, nasopharynx, neck, ovary, prostate, skin, stomach, testis, tongue, or uterus cancer. Furthermore additional anticancer therapies may be used in combination or in conjunction with methods of the invention. Such additional therapies may be administered before, after or concomitantly with methods of the invention. For example an additional anticancer therapy may be a chemotherapy, surgical therapy, an immunotherapy or a radiation therapy.

It is contemplated that DN RTEF-1 compositions of the invention may be administered to a patient locally or systemically. For example, methods of the invention may involve administering a DN RTEF-1 composition topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, intraperitoneally, subcutaneously, subconjunctival, intravesicularlly, mucosally, intrapericardially, intraumbilically, intraocularally, orally, by inhalation, by injection, by infusion, by continuous infusion, by localized perfusion bathing target cells directly, via a catheter, or via a lavage. As described supra in some cases a DN RTEF-1 composition is delivered to the eye, administration may be, for example, via topical, subconjunctival, periocular, retrobulbar, subtenon, intracameral, intravitreal, intraocular, subretinal, posterior juxtascleral or suprachoroidal administration. In certain aspects a DN RTEF-1 composition may be administered locally to the eye by intraocular injection, topical administration (e.g., in an eye drop formulation).

In some further embodiments there is provided a pharmaceutical composition of the invention comprised in a bottle said bottle comprising an exit portal that enables drop-wise administration of the composition. In some cases, a pharmaceutical composition comprised in a bottle comprises multiple doses however in certain aspects a bottle comprises a single dose unit for administration to one or two eyes, preferable a single dose unit is comprised in 1-2 drops of the formulation. As used herein the term "bottle" refers to any fluid container such as an ampoule, dropper or syringe.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

FIG. 1A, A schematic representation of the RTEF-1 splice variants identified by RT-PCR. Exon sequence for the untranslated region (diagonal hatching) and amino acid coding region (open boxes) of each splice variant is shown. Putative RTEF-1 functional domains are also diagramed, checkered box indicates the TEA DNA binding domain (asterisks show position of predicted α-helices), solid box indicates a nuclear localization signal (exon 4), vertical hatching indicates an activation domain (proline rich domain (PRD)) and horizontal hatching indicates the two STY domains in exons 9 and 10. FIG. 1B, A reproduction of agarose gel electrophoresis showing RTEF-1 specific RT-PCR products prepared from primary cultures of human retinal vascular endothelial cells (RVEC). Lanes 1 & 4: DNA ladder; Lane 2: cDNA prepared from RVEC under normoxic conditions gave 2 products (1305 & 936 bp in size); Lane 3: cDNA prepared from RVEC under hypoxic conditions gave 3 products (1305, 936 & 447 bp in size).

FIG. 5A-C: Detection of RTEF-1 polypeptides. Antibodies were raised against an amino acid sequence unique to RTEF-1 but shared by each of the naturally occurring variants. FIG. 5A, is a amino acid alignment between a region of RTEF-1 and related transcription factors. The amino acid sequence used for antibody production is underlined. FIG. 5B, a reproduction of an immunoblot using anti-RTEF-1 antibodies. Cells lysates used for analysis were from cell transfected with a pcDNA empty vector (lanes 2 and 8) or a pcDNA expression vector for the 1305 bp (lanes 3, 9), 936 bp (lanes 4, 10), 651 bp (lanes 5, 11) or 447 bp (lanes 6, 11) RTEF-1 variant. Detection of the each RTEF-1 variant is indicated by the ellipses. Lanes 1 and 7 are molecular mass markers. Lanes 1-6 represent an overexposure of the image from lanes 7-12. FIG. 5C, a reproduction of an immunoblot using anti-RTEF-1 antibodies to detect the RTEF-1 variant from cells transfected with a pcDNA 651 bp RTEF-1 expression vector. The expected ~24 KDa polypeptide is indicated by the arrow.

FIG. 6A-B: Expression of RTEF-1 variants in the eye. FIG. 6A, a reproduction of an immunoblot showing RTEF-1 expression in normal primate eye tissue. Immunoblot analysis was performed on protein from retina (lane 1), choroid (lane 2) and iris (lane 3) tissue lysates. M indicates a molecular mass markers. FIG. 6B, a reproduction of an ethidium bromide stained agarose gel used to visualize semi-quantitative RT-PCR productions generated using RTEF-1 specific primers. Lane 1 shows results from CRAO retina RNA while lane 2 shows results from control retinal RNA.

FIG. 7A-D: Immunohistochemistry analysis of RTEF-1 expression in primate eye tissue. FIG. 7A-B, Strong staining for RTEF-1 appears localized to iris (I), ciliary body (CB), optic nerve (ON) and retina (R). The cornea (C) and lens (L) were negative for RTEF-1 antibody hybridization. FIG. 7C-D, The strongest RTEF-1 staining is in the ganglion cell layer (GCL) and the inner nuclear layer (INL). Staining appears to be localized to both the cytoplasm and nucleus. Staining is scarce in the outer layers.

DETAILED DESCRIPTION OF THE INVENTION

Recently a number of strategies have been developed to inhibit angiogenic signaling for the purpose treating cancer and angiogenic disorders such as AMD. In particular, a number of strategies have focused on blockade of VEGF signaling by inhibiting the binding of VEGF with one or both of its cell surface receptors. However, these strategies are unable to address the initial production of VEGF that initiates aberrant angiogenesis. Thus, new methods and compositions that inhibit VEGF production may provide new methods for VEGF blockade and treatments for resultant angiogenesis. To this end, in certain aspects, the instant invention provides a dominant negative transcription factor that is integral in VEGF activation. Furthermore, since the instant invention concerns the targeting of an intracellular processes, therapeutics of the invention may be targeted to specific cell types thereby reducing undesirable systemic side effects. Thus, the instant inventions offers new methods to treat angiogenic disorders and/or ways to enhance the effectiveness of current VEGF blockade strategies.

Figure 1:
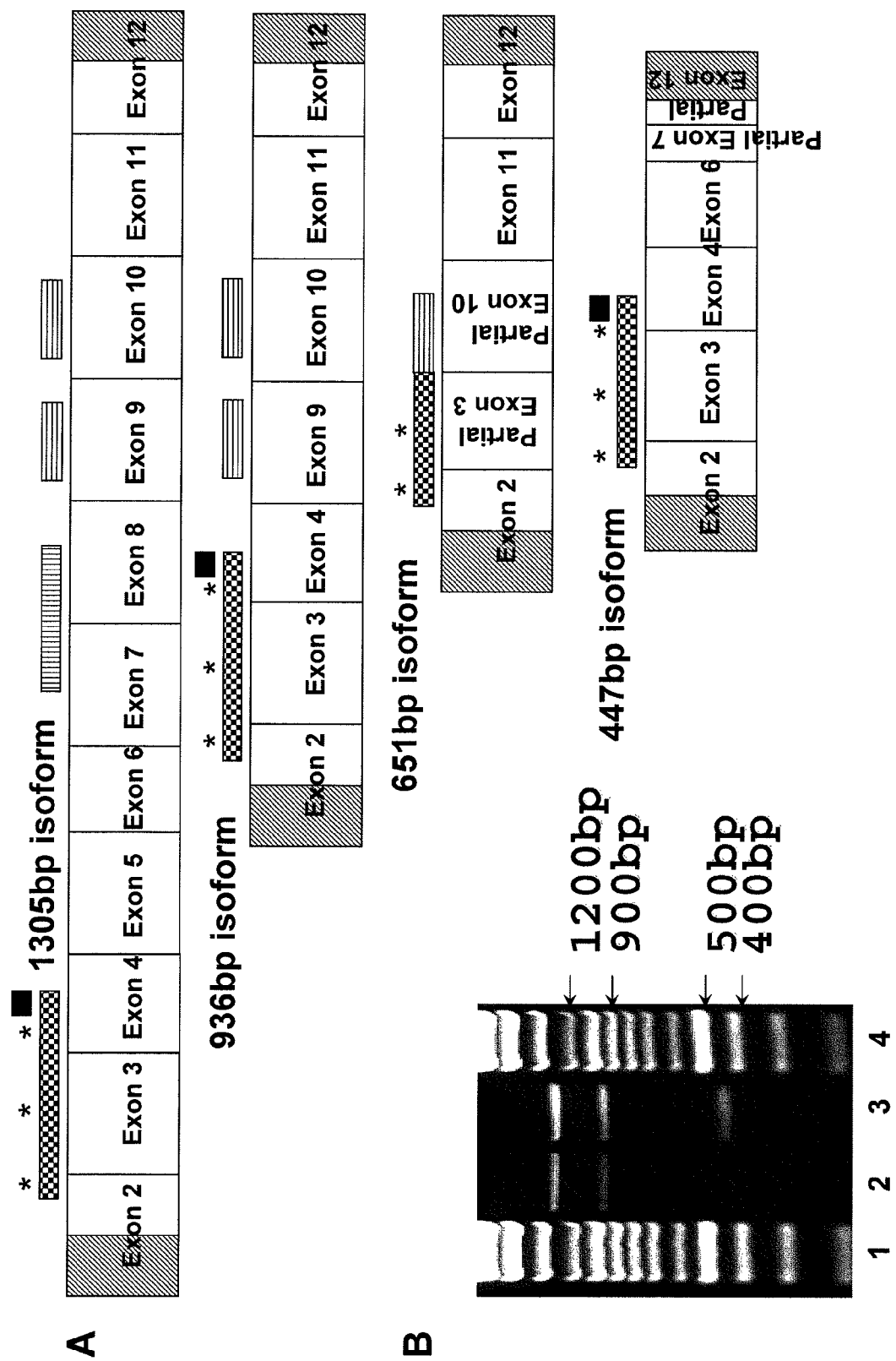
FIG. 1A-B: RTEF-1 mRNA splicing is altered during hypoxia. Retinal and iris endothelial cells were placed under hypoxic conditions and RTEF-1 splicing was analyzed by RT-PCR.
Figure 2:
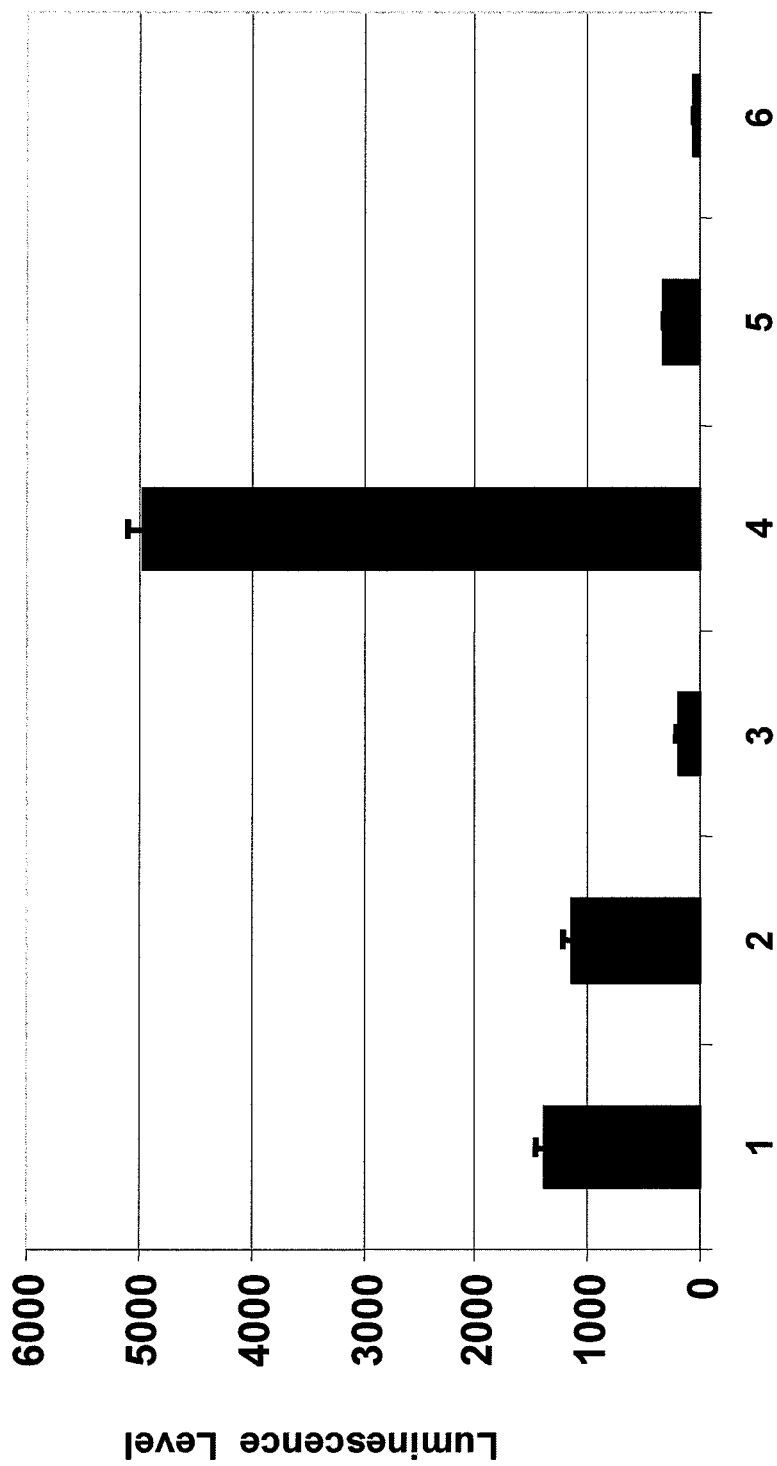
FIG. 2: RTEF-1 variants activate or repress the VEGF promoter. 293T cells were transfected with VEGF promoter reporter construct (VEGF promoter driving secreted alkaline phosphatase) along with an expression vector comprising the indicated RTEF-1 variant. Results show AP activity in the media was 6 hours post transfection with pSEAP-VEGF promoter plus pcDNA expression constructs comprising the 1305 bp (lane 1), 936 bp (lane 2), 651 bp (lane 3), ss-651-RMR bp (lane 6) or 447 bp (lane 4) RTEF-1 variants. Lane five shows control VEGF promoter activity when cotransfected with an insert-less pcDNA control plasmid.
Figure 4:
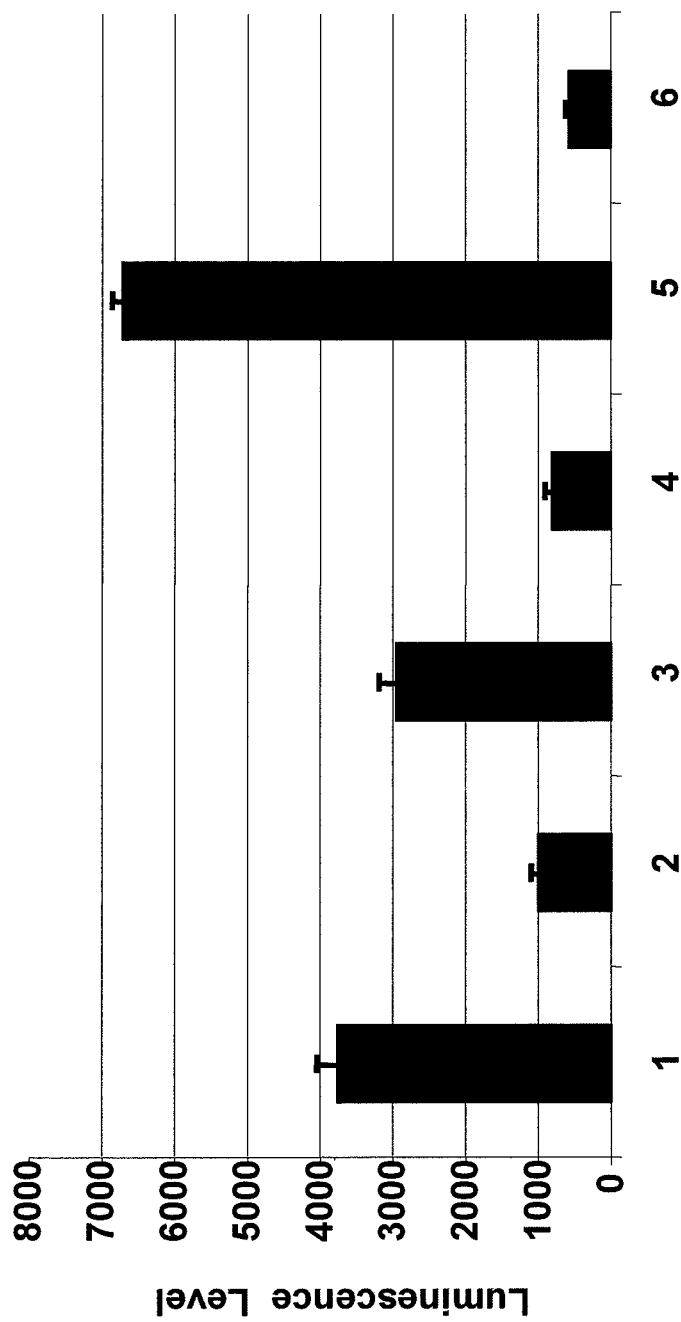
FIG. 4: The 651 bp RTEF-1 acts as a dominant negative. Cells were transfected as described above with pSEAP-VEGF and the 1305 bp (lanes 1, 2), the 936 bp (lanes 3, 4) or the 447 bp (lane 5, 6) RTEF-1 variant either alone (lanes 1, 3 and 5) or in addition to the ss-651-RMR bp RTEF-1 variant (lanes 2, 4 and 6).

RTEF-1 a member of a family of multifunctional transcription factors and has been shown to be an activator of VEGF transcription, including hypoxia induced VEGF transcription. However, as shown herein, multiple splice variants of RTEF-1 are produced in cells and RTEF-1 polypeptides produced from alternative RNA splice variants comprise altered transcriptional function (FIG. 1A, B). It particular, one RTEF-1 transcript of approximately 651 base pairs produces a polypeptide that inhibits VEGF promoter activity (FIG. 2, compare lanes 3 and 5). Furthermore, this RTEF-1 variant was shown to be an even more effective inhibitor of the VEGF promoter when provided as a fusion protein with a secretion signal and cell internalization polypeptide FIG. 2 lane 6). Importantly, as shown in FIG. 4 the polypeptide from the 651 bp RTEF-1 transcript acts in a dominant negative. That is the polypeptide not only reduces VEGF promoter activity but also blocks VEGF promoter enhancement by a other RTEF-1 protein isoforms. Furthermore, as shown in FIGS. 6 and 7 RTEF is expressed in the tissues of the eye thereby implicating its importance in the development of ocular neovascular disorders. Studies here indicate that RTEF-1 activation of VEGF production may for one factor that contributes to the development of neovascular disorders. Thus, methods and compositions of the invention may provide a means for preventing the early stages of neovascularization.

The instant invention provides the basis for new DN RTEF-1 polypeptides and the use thereof to prevent or inhibit angiogenic disorders. DN RTEF-1 polypeptides may delivered directly to the intra cellular milieu or expressed in targeted cells to blockade VEGF production. Such dominate negative polypeptides down regulate not only nascent VEGF production but also production of VEGF that is normally stimulated by RTEF-1 such as during hypoxia. Thus, compositions of the invention, may be used to reduce the ability of targeted cells and tissues to recruit new blood vessel formation. This is of great interest in, for example, ocular neovascular disorders such as AMD where the invasion of blood vessels is directly related to the pathogenesis of the disease. Furthermore, DN RTEF-1 may be used to treat tumors or tumor metastases by reducing their ability to gain nutrients through new blood vessel formation. Thus, methods to slow tumor growth and/or induce tumor regression are also provided. Furthermore, since compositions of the invention target intracellular transcription apprentice compositions of the invention may be used to target effected tissues by used of specific cell targeting/internalization moieties thereby reducing the side effects in other non-targeted tissues.

I. Dominate Negative RTEF-1 Polypeptides

A number of RTEF-1 variants are described and functionally characterized herein. For example, the four sequence specifically studied here comprise the following amino acid sequences.

SEQ ID NO: 1, encoded by a 1305 bp RTEF-1 human cDNA is a 434 amino acid protein having the sequence:

LEGTAGTITSNEWSSPTSPEGSTASGGSQALDKPIDNDGEGVWSPDIEQS

FQEALAIYPPCGRRKIILSDEGKMYGRNELIARYIKLRTGKTRTRKQVSS

HIQVLARRKAREIQAKLKDQAAKDKALQSMAAMSSAQIISATAFHSSMRL

ARGPGRPAVSGFWQGALPGQAETSHDVKPFSQQTYAQPPLPLPGFESPAG

PAPSPSAPPAPPWQGRRRGSSKLWMLEFSAFLEQQQDPDTYNKHLFVHIG

QSSPSYLRPYLEAVDIRQIYDKFPEKKGGLKDLFERGPSNAFFLVKFWAD

LNTNIEDEGSSFYGVSSQYESPENMIITCSTKVCSFGKQVVEKVETEYAR

YENGHYSYRIHRSPLCEYMINFIHKLKHLPEKYMMNSVLENFTILQVVTN

RDTQETLLCIAYVFEVSASEHGAQHHIYRLVKE

SEQ ID NO: 2, encoded a 936 bp human cDNA is a 311 amino acid protein having the sequence:

LEGTAGTITSNEWSSPTSPEGSTASGGSQALDKPIDNDGEGVWSPDIEQS

FQEALAIYPPCGRRKIILSDEGKMYGRNELIARYIKLRTGKTRTRKQVSS

HIQVLARRKAREIQAKLKYNKHLFVHIGQSSPSYLRPYLEAVDIRQIYDK

FPEKKGGLKDLFERGPSNAFFLVKFWADLNTNIEDEGSSFYGVSSQYESP

ENMIITCSTKVCSFGKQVVEKVETEYARYENGHYSYRIHRSPLCEYMINF

IHKLKHLPEKYMMNSVLENFTILQVVTNRDTQETLLCIAYVFEVSASEHG

AQHHIYRLVKE

SEQ ID NO: 3, encoded by a 651 bp human cDNA is a 216 amino acid protein having the sequence:

LEGTAGTITSNEWSSPTSPEGSTASGGSQALDKPIDNDGEGVWSPDIEQS

FQEALAIYPPCGRRKIILSDEGKMYGRNELIARYIKLRTGKTSSFYGVSS

QYESPENMIITCSTKVCSFGKQVVEKVETEYARYENGHYSYRIHRSPLCE

YMINFIHKLKHLPEKYMMNSVLENFTILQVVTNRDTQETLLCIAYVFEVS

ASEHGAQHHIYRLVKE

SEQ ID NO: 4, encoded by a 447 bp human cDNA is a 148 amino acid protein having the sequence:

LEGTAGTITSNEWSSPTSPEGSTASGGSQALDKPIDNDGEGVWSPDIEQS

FQEALAIYPPCGRRKIILSDEGKMYGRNELIARYIKLRTGKTRTRKQVSS

HIQVLARRKAREIQAKLKFWQGALPGQAETSHDVKPFSQHHIYRLVKE

As described supra, in certain aspects of the invention a dominant negative (DN) RTEF-1 polypeptide may comprise one or more internal amino acid deletions. For example, in some cases DN RTEF-1 may comprise a deletion of amino acids encoded by exons 3, 4, 5, 6, 7, 8, 9 or 10. For example, in certain aspects a DN-RTEF1 comprises the amino acid sequence of SEQ ID NO:3 or a derivative thereof.

TABLE 1

RTEF-1 amino acid sequence by encoding exon

| Exon | Amino acid sequence encoded |
|---|---|
| 1 | N/A |
| 2 | LEGTAGTITSNEWSSPTSPEGSTASGGSQALDKPIDNDAEGVWS PDIEQSFQEALAIYPPCGRRKIILSDEGKMY<u>G</u>* (SEQ ID NO: 5) |
| 3 | RNELIARYIKLRTGKTRTRKQ (SEQ ID NO: 6) |
| 4 | VSSHIQVLARRKAREIQAKLK (SEQ ID NO: 7) |
| 5 | DQAAKDKALQSMAAMSSAQIISATAFHSSMALARGPGRPAVSG (SEQ ID NO: 8) |
| 6 | FWQGALPGQAGTSH<u>D</u>* (SEQ ID NO: 9) |
| 7 | VKPFSQQTYAVQPPLPL<u>G</u>* (SEQ ID NO: 10) |
| 8 | FESPAGPAPSPSAPPAPPWQGRSVASSKLWMLEFSAFLEQQQDPDT (SEQ ID NO: 11) |
| 9 | YNKHLFVHIGQSSPSYSDPYLEAVDIRQIYDKFPEKKGGLKDLF ERGPSNAFFLVKFW (SEQ ID NO: 12) |
| 10 | ADLNTNIEDEGSSFYGVSSQYESPENMIITCSTKVCSFGKQVVE KVE (SEQ ID NO: 13) |
| 11 | TEYARYENGHYSYRIHRSPLCEYMINFIHKLKHLPEKYMMNSVL ENFTILQ (SEQ ID NO: 14) |
| 12 | VVTNRDTQETLLCIAYVFEVSASEHGAQHHIYRLVKE (SEQ ID NO: 15) |

*Indicates amino acid that are encoded by nucleic acid codons that are split between exons.

In additional aspects of the invention, DN RTEF-1 polypeptides may be further modified by one or more amino substitutions while maintaining their transcriptional functions. For example, amino acid substitutions can be made at one or more positions wherein the substitution is for an amino acid having a similar hydrophilicity. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in an RTEF-1 sequence and will likely only have minor effects on their activity and ability to repress VEGF promoter activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the DN RTEF-1 polypeptides described herein may be modified by the substitution of an amino acid, for different, but homologous amino acid with a similar hydrophilicity value. Amino acids with hydrophilicities within +/−1.0, or +/−0.5 points are considered homologous.

II. Cell Internalization and Targeting Moieties

Cell internalization moieties for use herein may be any molecule in complex (covalently or non-covalently) with a DN RTEF-1 that mediate transport of the DN RTEF-1 across a cell membrane. Such internalization moieties may be peptides, polypeptides, hormones, growth factors, cytokines, aptamers or avimers. Furthermore, cell internalization moiety may mediate non-specific cell internalization or be a cell targeting moiety that is internalized in a subpopulation of targeted cells.

For example, in certain embodiments, cell targeting moieties for use in the current invention are antibodies. In general the term antibody includes, but is not limited to, polyclonal antibodies, monoclonal antibodies, single chain antibodies, humanized antibodies, minibodies, dibodies, tribodies as well as antibody fragments, such as Fab', Fab, F(ab')2, single domain antibodies and any mixture thereof. In some cases it is preferred that the cell targeting moiety is a single chain antibody (scFv). In a related embodiment, the cell targeting domain may be an avimer polypeptide. Therefore, in certain cases the cell targeting constructs of the invention are fusion proteins comprising a DN RTEF-1 and a scFv or an avimer. In some very specific embodiments the cell targeting construct is a fusion protein comprising DN RTEF-1 polypeptide fused to a single chain antibody.

In certain aspects of the invention, a cell targeting moieties may be a growth factor. For example, transforming growth factor, epidermal growth factor, insulin-like growth factor, fibroblast growth factor, B lymphocyte stimulator (BLyS), heregulin, platelet-derived growth factor, vascular endothelial growth factor (VEGF), or hypoxia inducible factor may be used as a cell targeting moiety according to the invention. These growth factors enable the targeting of constructs to cells that express the cognate growth factor receptors. For example, VEGF can be used to target cells that express FLK-1 and/or Flt-1. In still further aspects the cell targeting moiety may be a polypeptide BLyS (see U.S. Appln. 20060171919).

In further aspects of the invention, a cell targeting moiety may be a hormone. Some examples of hormones for use in the invention include, but are not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, insulin-like growth factor-1, leptin, thrombopoietin, angiotensinogen, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, or IL-36. As discussed above targeting constructs that comprise a hormone enable method of targeting cell populations that comprise extracellular receptors for the indicated hormone.

In yet further embodiments of the invention, cell targeting moieties may be cytokines. For example, IL1, IL2, IL3, IL4, IL5, IL6, IL7, IL8, IL9, IL10, IL11, IL12, IL13, IL14, IL15, IL-16, IL-17, IL-18, granulocyte-colony stimulating factor, macrophage-colony stimulating factor, granulocyte-macrophage colony stimulating factor, leukemia inhibitory factor, erythropoietin, granulocyte macrophage colony stimulating factor, oncostatin M, leukemia inhibitory factor, IFN-γ, IFN-α, IFN-β, LT-β, CD40 ligand, Fas ligand, CD27 ligand, CD30 ligand, 4-1BBL, TGF-β, IL 1α, IL-1β, IL-1 RA, MIF and IGIF may all be used as targeting moieties according to the invention.

In certain aspects of the invention a cell targeting moiety of the invention may be a cancer cell targeting moiety. It is well known that certain types of cancer cells aberrantly express surface molecules that are unique as compared to surrounding tissue. Thus, cell targeting moieties that bind to these surface molecules enable the targeted delivery of DN RTEF-1 specifically to the cancers cells. For example, a cell targeting moiety may bind to and be internalized by a lung, breast, brain, prostate, spleen, pancreatic, cervical, ovarian, head and neck, esophageal, liver, skin, kidney, leukemia, bone, testicular, colon or bladder cancer cell. The skilled artisan will understand that the effectiveness of cancer cell targeted DN RTEF-1 may, in some cases, be contingent upon the expression or expression level of a particular cancer marker on the cancer cell. Thus, in certain aspects there is provided a method for treating a cancer with targeted DN RTEF-1 comprising determining whether (or to what extent) the cancer cell expresses a particular cell surface marker and administering DN RTEF-1 targeted therapy (or another anticancer therapy) to the cancer cells depending on the expression level of a marker gene or polypeptide.

As discussed above cell targeting moieties according to the invention may be, for example, an antibody. For instance, a cell targeting moiety according the invention may bind to a skin cancer cell such as a melanoma cell. It has been demonstrated that the gp240 antigen is expressed in variety of melanomas but not in normal tissues. Thus, in certain aspects of the invention, there is provided a cell targeting construct comprising an DN RTEF-1 and a cell targeting moiety that binds to gp240. In some instances, the gp240 binding molecule may be an antibody, such as the ZME-018 (225.28S) antibody or the 9.2.27 antibody. In an even more preferred embodiment, the gp240 binding molecule may be a single chain antibody such as the scFvMEL antibody.

In yet further specific embodiments of the invention, cell targeting constructs may be directed to breast cancer cells. For example cell targeting moieties that bind to Her-2/neu, such as anti-Her-2/neu antibodies may conjugated to a DN RTEF-1. One example of a such a cell targeting constructs are fusion proteins comprising the single chain anti-Her-2/neu antibody scFv23 and DN RTEF-1. Other scFv antibodies such as scFv(FRP5) that bind to Her-2/neu may also be used in the compositions and methods of the current invention (von Minckwitz et al., 2005).

In certain additional embodiments of the invention, it is envisioned that cancer cell targeting moieties according to invention may have the ability to bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example are the cell targeting agents described in U.S. Appln. 2004005647 and in Winthrop et al., 2003 that bind to MUC-1 an antigen that is expressed on a variety cancer types. Thus, it will be understood that in certain embodiments, cell targeting constructs according the invention may be targeted against a plurality of cancer or tumor types.

III. Methods for Producing Antibodies

The following methods exemplify some of the most common antibody production methods.

A. Polyclonal Antibodies

Polyclonal antibodies generally are raised in animals by multiple subcutaneous (sc) or intraperitoneal (ip) injections of the antigen. As used herein the term "antigen" refers to any polypeptide that will be used in the production of a antibodies. Antigens for use according to the instant invention include in certain instances, cancer cell surface marker polypeptides and eye specific cell surface markers.

It may be useful to conjugate an antigen or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg of 1 µg of conjugate (for rabbits or mice, respectively) with 3 volumes of Freud's complete adjuvant and injecting the solution intradermally at multiple sites. One month later the animals are boosted with 1/5 to 1/10 the original amount of conjugate in Freud's complete adjuvant by subcutaneous injection at multiple sites. 7 to 14 days later the animals are bled and the serum is assayed for specific antibody titer. Animals are boosted until the titer plateaus. Preferably, the animal boosted with the same antigen conjugate, but conjugated to a different protein and/or through a different cross-linking reagent. Conjugates also can be made in recombinant cell culture as protein fusions. Also, aggregating agents such as alum are used to enhance the immune response.

B. Monoclonal Antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, monoclonal antibodies of the invention may be made using the hybridoma method first described by Kohler & Milstein (1975), or may be made by recombinant DNA methods (U.S. Pat. No. 4,816,567).

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding 1986).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against the target antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard (1980).

After hybridoma cells are identified that produce antibodies of the desired specificity, affinity, and/or activity, the clones may be subcloned by limiting dilution procedures and grown by standard methods, Goding (1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al. (1984), or by covalently joining to the immunoglobulin coding sequence all or part of the coding sequence for a non-immunoglobulin polypeptide. In that manner, "chimeric" or "hybrid" antibodies are prepared that have the binding specificity for any particular antigen described herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for the target antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^3H$, $^{14}C$, $^{32}P$, $^{35}S$, or $^{125}I$, or an enzyme, such as alkaline phosphatase, beta-galactosidase or horseradish peroxidase.

Any method known in the art for separately conjugating the antibody to the detectable moiety may be employed, including those methods described by Hunter et al. (1962); David et al. (1974); Pain et al. (1981); and Nygren (1982).

The antibodies of the present invention may be employed in any known assay method, such as competitive binding assays, direct and indirect sandwich assays, and immunoprecipitation assays (Zola, 1987).

Competitive binding assays rely on the ability of a labeled standard (which may be a purified target antigen or an immunologically reactive portion thereof) to compete with the test sample analyte for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

C. Humanized Antibodies

As discussed previously, antibodies for use in the methods of the invention may be polyclonal or monoclonal antibodies or fragments thereof. However, in some aspects it is preferred that the antibodies are humanized such that they do not illicit an immune response in subject being treated. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., 1986); Riechmann et al., 1988; Verhoeyen et al., 1988), by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties, for example the ability bind to an be internalized by a target cell. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

D. Human Antibodies

Human monoclonal antibodies can be made by the hybridoma method. Human myeloma and mouse-human heteromyeloma cell lines for the production of human monoclonal antibodies have been described, for example, by Kozbor (1984) and Brodeur et al. (1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g. Jakobovits et al. (1993); Jakobovits et al. (1993).

Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson et al. (1993). Several sources of V-gene segments can be used for phage display. Clackson et al. (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al. (1991), or Griffith et al. (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al. (1993), and the isolation of a high affinity human antibody directly from such large phage library has been reported. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

IV. Nucleic Acid Molecules

In certain aspects, the instant invention concerns nucleic acid molecules encoding a DN RTEF-1 polypeptide. In certain aspects, a DN RTEF-1 nucleic acid sequence is comprised in a nucleic acid vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et. al., 1998), murine epididymal retinoic acid-binding gene (Lareyre et. al., 1999), human CD4 (Zhao-Emonet et. al., 1998), mouse alpha2 (XI) collagen (Tsumaki, et. al., 1998), D1A dopamine receptor gene (Lee, et. al., 1997), insulin-like growth factor II (Wu et. al., 1997), and human platelet endothelial cell adhesion molecule-1 (Almendro et. al., 1996).

B. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

C. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et. al., 1999, Levenson et. al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

D. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et. al., 1997, herein incorporated by reference).

E. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences. In certain specific cases a polyadenylation signal may be the signal from neuropilin-1 as described in U.S. Appln. 20050175591.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

F. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

G. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

H. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, *E. coli* LE392.

Further useful plasmid vectors include pIN vectors (Inouye et. al., 1985); and pGEX vectors, for use in generating glutathione S transferase (GST) soluble fusion proteins for later purification and separation or cleavage. Other suitable fusion proteins are those with β galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

I. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). DN RTEF-1 components of the present invention may be a viral vector that encodes a DN RTEF-1 polypeptide. Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et. al., 1992; Curiel, 1994). Adeno associated virus (AAV) is an attractive vector system for use in the delivery of DN RTEF-1 expression cassettes of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et. al., 1984; Laughlin et. al., 1986; Lebkowski et. al., 1988; McLaughlin et. al., 1988). Details concerning the generation and use of rAAV vectors are described in U.S. Pat. Nos. 5,139,941 and 4,797,368, each incorporated herein by reference.

3. Retroviral Vectors

Retroviruses have promise as DN RTEF-1 delivery vectors in therapeutics due to their ability to integrate their genes into the host genome, transferring a large amount of foreign genetic material, infecting a broad spectrum of species and cell types and of being packaged in special cell lines (Miller, 1992).

In order to construct a DN RTEF-1 retroviral vector, a nucleic acid (e.g., one encoding a DN RTEF-1) is inserted into the viral genome in the place of certain viral sequences to produce a virus that is replication defective. In order to produce virions, a packaging cell line containing the gag, pol, and env genes but without the LTR and packaging components is constructed (Mann et. al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et. al., 1983). The media containing the recombinant retroviruses is then collected, optionally concentrated, and used for gene transfer. Retroviral vectors are able to infect a broad variety of cell types. However, integration and stable expression require the division of host cells (Paskind et. al., 1975).

Lentiviruses are complex retroviruses, which, in addition to the common retroviral genes gag, pol, and env, contain other genes with regulatory or structural function. Methods for delivery of antiangiogenic molecules with lentiviral vectors have been previously described, see for example U.S. Pat. No. 7,122,181 incorporated herein by reference. Lentiviral vectors are well known in the art (see, for example, Naldini et. al., 1996; Zufferey et. al., 1997; Blomer et. al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present invention. Vectors derived from viruses such as vaccinia virus (Ridgeway, 1988; Baichwal and Sugden, 1986; Coupar et. al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et. al., 1988; Horwich et. al., 1990).

5. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et. al., 1989). Using antibodies against major histocompatibility complex class I and class II antigens, they demonstrated the infection of a variety of human cells that bore those surface antigens with an ecotropic virus in vitro (Roux et. al., 1989).

J. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et. al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et. al., 1986; Potter et. al., 1984); by calcium phosphate precipitation (Graham and Van Der Eb, 1973; Chen and Okayama, 1987; Rippe et. al., 1990); by using DEAE dextran followed by polyethylene glycol (Gopal, 1985); by direct sonic loading (Fechheimer et. al., 1987); by liposome mediated transfection (Nicolau and Sene, 1982; Fraley et. al., 1979; Nicolau et. al., 1987; Wong et. al., 1980; Kaneda et. al., 1989; Kato et. al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et. al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et. al., 1993; U.S. Pat. Nos. 4,684,611 and 4,952,500, each incorporated herein by reference); by desiccation/inhibition mediated DNA uptake (Potrykus et. al., 1985), and any combination of such methods. Through the application of techniques such as these, organelle(s), cell(s), tissue(s) or organism(s) may be stably or transiently transformed.

V. Therapeutic Methods

A. Pharmaceutical Preparations

Therapeutic compositions for use in methods of the invention may be formulated into a pharmacologically acceptable format. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one DN RTEF-1 polypeptide or nucleic acid active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In particular embodiments, the compositions of the present invention are suitable for application to mammalian eyes. For example, the formulation may be a solution, a suspension, or a gel. In some embodiments, the composition is administered via a bioerodible implant, such as an intravitreal implant or an ocular insert, such as an ocular insert designed for placement against a conjunctival surface. In some embodiments, the therapeutic agent coats a medical device or implantable device.

In preferred aspects the formulation of the invention will be applied to the eye in aqueous solution in the form of drops. These drops may be delivered from a single dose ampoule which may preferably be sterile and thus rendering bacteriostatic components of the formulation unnecessary. Alternatively, the drops may be delivered from a multi-dose bottle which may preferably comprise a device which extracts preservative from the formulation as it is delivered, such devices being known in the art.

In other aspects, components of the invention may be delivered to the eye as a concentrated gel or similar vehicle which forms dissolvable inserts that are placed beneath the eyelids.

Furthermore, the therapeutic compositions of the present invention may be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired. Thus, in some case dosages can be determined by measuring for example changes in serum insulin or glucose levels of a subject.

Precise amounts of the therapeutic composition may also depend on the judgment of the practitioner and are peculiar to each individual. Factors affecting the dose include the physical and clinical state of the patient, the route of administration, the intended goal of treatment (e.g., alleviation of symptoms versus attaining a particular serum insulin or glucose concentration) and the potency, stability and toxicity of the particular therapeutic substance.

In particular embodiments, the compositions of the present invention are suitable for application to mammalian eyes. For example, the formulation may be a solution, a suspension, or a gel. In some embodiments, the composition is administered via a bioerodible implant, such as an intravitreal implant or an ocular insert, such as an ocular insert designed for placement against a conjunctival surface. In some embodiments, the therapeutic agent coats a medical device or implantable device.

In preferred aspects the formulation of the invention will be applied to the eye in aqueous solution in the form of drops. These drops may be delivered from a single dose ampoule which may preferably be sterile and thus rendering bacteriostatic components of the formulation unnecessary. Alternatively, the drops may be delivered from a multi-dose bottle which may preferably comprise a device which extracts preservative from the formulation as it is delivered, such devices being known in the art.

In other aspects, components of the invention may be delivered to the eye as a concentrated gel or similar vehicle which forms dissolvable inserts that are placed beneath the eyelids.

B. Additional Therapies

As discussed supra in certain aspects therapeutic methods of the invention may be used in combination or in conjunction with additional antiangiogenic or anticancer therapies.

1. Chemotherapy

In certain embodiments of the invention DN RTEF-1 is administered in conjunction with a chemo therapeutic agent. For example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, gemcitabien, navelbine, farnesyl-protein transferase inhibitors, transplatinum, 5-fluorouracil, vincristin, Velcade, vinblastin and methotrexate, or any analog or derivative variant of the foregoing may used in methods according to the invention.

2. Radiotherapy

In certain further embodiments of the invention DN RTEF-1 compositions may be used to sensitize cell to radiation therapy. Radio therapy may include, for example, γ-rays, X-rays, and/or the directed delivery of radioisotopes to tumor cells. In certain instances microwaves and/or UV-irradiation may also used according to methods of the invention. Dosage ranges for X-rays range from daily doses of 50 to 200 roentgens for prolonged periods of time (3 to 4 wk), to single doses of 2000 to 6510 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radio therapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B, Her-2/neu, gp240 and p155.

4. Genes

In yet another embodiment, gene therapy in which a therapeutic polynucleotide is administered before, after, or at the same time as a cell targeting construct of the present invention. Delivery of DN RTEF-1 in conjunction with a vector encoding one or more additional gene products may have a combined anti-hyperproliferative effect on target tissues. A variety of genes are encompassed within the invention, for example a gene encoding p53 may be delivered in conjunction with DN RTEF-1 compositions.

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. A DN RTEF-1 therapy of the invention may be employed alone or in combination with a cytotoxic therapy as neoadjuvant surgical therapy, such as to reduce tumor size prior to resection, or it may be employed as postadjuvant surgical therapy, such as to sterilize a surgical bed following removal of part or all of a tumor.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Agents

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Experimental Methods

Primary Ocular Vascular Endothelial Cell Isolation and Culture

All use of human cells and tissue was in accordance with approved institutional review board protocols. Primary cultures of endothelial cells isolated from human retina were established using established protocols and used as a source for mRNA (Kanda et al., 1998; Silverman et al., 2005). Human cadaver eyes were obtained from anonymous donors (Lion's Eye Bank, Portland, Oreg.) within 24 hours of death. Donors had no history of cardiovascular or ocular disease and ranged in age from 16-42. Briefly, these retinal and iris tissues were aseptically dissected and separated away from donor eyes, and digested in 0.2% collagenase (Sigma Chemical Co, St Louis, Mo.) and endothelial cells (EC) were isolated from other cell types by using mouse monoclonal anti-human CD31 antibody-coated magnetic beads (Dynal Biotech, Inc., Lake Success, N.Y.). ECs were cultured in complete MCDB-131 medium (Clonetics/BioWhittaker, Walkersville, Md.) supplemented with 10% fetal bovine serum and antibiotics. Cells were used at passages 2 to 5. After 2 rounds of magnetic bead separation the EC cultures were more than 99.5% pure, as evaluated by morphologic criteria, expression of CD31 and von Willebrand factor, and uptake of acetylated low density lipoprotein (Silverman et al., 2005).

Induction of Hypoxia.

Retinal and iris endothelial cells were cultured to 80% confluence in 60 mm diameter culture dishes and then placed in an air tight Modulator Incubator Chamber (Billups-Rothenberg, Del Mar, Calif.). A 1% $O_2$, 5% $CO_2$ and remainder $N_2$ gas mix was flushed through the chamber for exactly 5 minutes whereupon the chamber was sealed and placed into a humidified 37° C. incubator. After 8 hours the chamber was flushed again for 5 minutes with the hypoxic gas mix and sealed and incubated for a further 8 hours and then flushed again and incubated for another 8 hours at which point total RNA was isolated.

Total RNA Extraction and RT-PCR

Total RNA was isolated using an RNAqueous kit (Ambion Inc, Austin, Tex.) according to manufacturer's protocol and 50 ng of this RNA was used with an oligo-dT primer first strand synthesis (SuperScript II, Stratagene, La Jolla, Calif.). The following primers, F1: 5'-ttggagggcacggccggca-3' (SEQ ID NO:20) and R1: 5'-tcattctttcaccagcctgta-3' (SEQ ID NO:21) designed from published RTEF-1 sequence (NCBI accession # U63824) was used for second strand PCR amplification using standard conditions. Amplified products were subjected to electrophoresis and visualized in a 1.5% agarose gel and subsequently purified from the gel (Qiaquick Gel Extraction, Qiagen, Valencia, Calif.) for standard dideoxynucleotide sequencing on an Abi 310 automated sequencer.

Reporter Gene Analysis

Full length RTEF-1 isoforms were directionally cloned into the pcDNA 3.1 expression plasmid (Invitrogen, Carlsbad, Calif.). The predicted TTG start was converted to ATG within the forward primer sequence. Human VEGF 5' proximal promoter fragment of 1,136 bp containing 54 bp of 5'UTR and 1,082 bp upstream of the transcription start site was directionally cloned 5' to the secretable alkaline phosphatase (SEAP) gene within the pSEAP reporter plasmid (Clontech, Mountain View, Calif.). Promoter fragments with deletions were constructed by first amplifying the 5' end of the promoter and 3' end of the promoter and subsequent ligation of the amplified products. The ligated products lacking the region of interest were then amplified and directionally cloned into the promoterless pSEAP vector. All constructs were sequenced on both strands for verification prior to transfection studies.

Transfection Assays.

Transfection was performed using the Amaxa Nucleofection Device (Amaxa Inc, Gaithersburg, Md.), Amaxa reagents and standard manufacturer's protocol. Briefly, 293T cells were cultured in 10% DMEM media till 80% confluent, trypsinized and collected. One million cells was used per nucleofection. One million cells were resuspended in 100 ul of Nucleofect solution and 5 µl (containing 2 µg) of total plasmid DNA, electroporated (program #A023 on Nucleofection Device) and then immediately resuspended in 1 ml of prewarmed media and seeded into a single well of a 6 well plate. Cells were allowed to recover for 16-18 hours and the media was carefully removed and replaced with exactly 500 ml of fresh media. After exactly 6 hours of incubation 150 µl of media was carefully removed and 25 µl of this was either assayed immediately or stored at −20° C. for future SEAP analysis. Three separate 25 µl media aliquots were used for SEAP analysis according to manufacturer's protocol (BD Biosciences, San Jose, Calif.) and the SEAP value for all 3 readings were averaged for comparison to triplicate repeat experiments.

Each cotransfection was repeated at least 3 times in a single experiment and each experiment repeated again independently 2 more times with separate plasmid preparations (n=9-12). One representative experiment is presented in figures. Statistical analysis was performed using a Student's t-test (two-tailed) to compare the 3 or 4 samples in a single experiment. Bonferroni correction for multiple testing was applied and a $P<0.01$ was considered as significant.

For each cotransfection assay (when 2 plasmids were transfected together in the same tube) the copy number of each plasmid was adjusted to be equivalent to the copy number of the largest plasmid used. The pSEAP vector without a promoter and the pcDNA 3.1 expression plasmid with no insert served as negative controls. For each nucleofection experiment 2 separate positive control plasmids, a SV40 promoter pSEAP plasmid and a pGFPmax vector, were transfected at the same time to ensure efficient and equal transfection efficiencies. The pSEAP plasmid with an SV40 promoter served as a positive control for subsequent SEAP protein analysis. The pGFPmax vector also served as positive control for transfection for each batch of cells allowing visual confirmation of consistent transfection efficiency. Nucleofection consistently gave 80-90% transfection efficiency in 293T cells in all experiments.

Example 2

Novel Isoforms of RTEF-1 Exist within Hypoxic and Normal Ocular Vascular Endothelial Cells Amplification from cDNA prepared from primary cultures of human retinal (PRVEC) and iris (PIVEC) vascular endothelial cells, using the F1 and R1 primer pair, gave products of approximately 1305 bp and 936 bp (FIG. 1B). Using the same primer pair amplification from cDNA isolated from PRVEC that had been cultured under hypoxic conditions for 24 hours, prior to isolation of mRNA, gave an additional product of approximately 447 bp (FIG. 1B). The 651 bp cDNA was isolated from Human primary retinal vascular endothelial cells (PRVEC).

Sequencing analysis revealed that the largest product was identical to the full length 1305 bp RTEF-1 gene spanning from the start to the stop codon (SEQ ID NO:1), whereas the 936 bp, 651 bp and 447 bp transcripts were alternate spliced transcripts of the 1305 bp product. The following description of codons will be numbered according to the sequence in the 1305 bp transcript which consists of 435 codons with the protein initiating codon being 1 and the stop codon being 435. Exons 5 to 8, four of the eleven exons that are predicted to code for the protein portion of the 1305 bp transcript, are spliced out of the 936 bp version (FIG. 1A). Not only is exon 5 lacking in the 447 bp isoform, but an unusual in frame splice event occurs in the middle of exon 7 which splices out from Gln-83 in exon 7 to codon Gln-425 within exon 12 (FIG. 1A). In the case of the 651 bp isoform a 5' portion of exon 3 is spliced directly into an internal splice acceptor site in exon 10 thereby completely removing exons 4, 5, 6, 7, 8 and 9 from the transcript.

The 1305 bp product shows identity to the transcriptional enhancer factor-1 related (RTEF-1) gene originally identified in human cardiac, skeletal muscle, pancreas and lung tissue (Stewart et al., 1996). Two other RTEF isoforms, variant 2 (accession #NM_201441) which lack exon 5 from Asp-119 to Gly-161 and variant 3 (accession #NM_201443) which employs a downstream protein initiation site at Met-130, have previously been reported. The 936 bp, 651 bp and 447 bp isoforms identified within human ocular vascular cells have not been identified in any other human tissue to date.

The full length 1305 bp transcript encodes a polypeptide having 434 amino acids with a predicted molecule weight of ~48.6 KDa. This polypeptide comprises 50 strongly basic (K,R), 47 strongly acidic (D,E), 133 hydrophobic (A, I, L, F, W, V) and 124 polar (N, C, Q, S, T, Y) amino acids. The predicted isoelectric point is 8.248 and the predicted charge is 4.799 at pH 7.0. Each of the identified RTEF-1 isoforms appear to utilize a non-canonical TTG (UUG) start codon resulting in an amino terminal lysine residue.

The 936 bp transcript encodes a polypeptide having 311 amino acids with a predicted molecule weight of ~35.6 KDa. This polypeptide comprises 40 strongly basic (K,R), 38 strongly acidic (D,E), 93 hydrophobic (A, I, L, F, W, V) and 92 polar (N, C, Q, S, T, Y) amino acids. The predicted isoelectric point is 8.037 and the predicted charge is 3.458 at pH 7.0.

The 651 bp transcript encodes a polypeptide having 216 amino acids with a predicted molecule weight of ~24.4 KDa. This polypeptide comprises 22 strongly basic (K,R), 27 strongly acidic (D,E), 60 hydrophobic (A, I, L, F, W, V) and 71 polar (N, C, Q, S, T, Y) amino acids. The predicted isoelectric point is 6.039 and the predicted charge is −4.046 at pH 7.0. The 651 bp isoform is spliced in frame from within exon 3 after Thr-92 into the middle of exon 10 at Ser-311 (all numbering based in the largest RTEF-1 isoform (SEQ ID NO:1)). Thus, the 651 bp isoform contains all of exon 2, most of exon 3 (lacks 5 of the 22 amino acids in exon 3), most of exon 10 (lacks the first 11 amino acids of exon 10) and complete exons 11 and 12. This results in retention of most of the TEA binding domain but with loss of one of the 3 predicted α-helices and the putative nuclear localization signal (Leu-105 to Lys-109) normally contained within the 72 amino acid TEA domain. The Proline Rich Domain (PRD), activation domain and the first STY domain (Ser-253 to Ser-271) is also lacking in the 651 bp isoform. Interestingly, the splice event into exon 10 starts at Ser-11 within this exon (i.e., the 11$^{th}$ amino acid in exon 10) which is the very start of the second STY domain (Ser-253 to Ser-336). This splice event results in fusion of a partial TEA domain, lacking a putative nuclear localization signal, directly with a STY domain.

The 447 bp transcript encodes a polypeptide having 148 amino acids with a predicted molecule weight of ~16.5 KDa. This polypeptide comprises 22 strongly basic (K,R), 17 strongly acidic (D,E), 43 hydrophobic (A, I, L, F, W, V) and 40 polar (N, C, Q, S, T, Y) amino acids. The predicted isoelectric point is 9.444 and the predicted charge is 5.561 at pH 7.0.

The predicted protein sequence for both the 936 bp and 447 bp isoforms contain the 72 amino acid TEA domain (Asp-38 to Lys-109) which contains 3 predicted α-helices and a putative nuclear localization signal (Leu-105 to Lys-109). However within the C-terminal domain a proline rich-domain (Pro-189 to Pro-213) spanning the last 6 amino acids of exon 7 and the first 19 residues of exon 8 is missing from the 447 bp isoform (FIG. 1A). In addition two STY domains (Ser-253 to Ser-271 and Ser-311 to Ser-336), a region rich with hydroxylated residues such as serine, threonine and tyrosine, one located within exon 9 and the other within exon 10 are also lacking in the 447 bp isoform (FIG. 1A).

Example 3

The Effects of Novel RTEF-1 Isoforms on Expression from the VEGF Promoter

It has been shown that the polypeptide resulting from the 1305 bp isoform acts as a transcriptional stimulator of VEGF, in bovine aortic endothelial cells, via binding to a Sp1 site (Shie et al., 2004). Thus, studies were conducted to investigate whether the new isoforms were also capable of stimulating expression from the human VEGF promoter. The 5' proximal promoter of the human VEGF gene, consisting of 54 bp of 5'UTR and 1,082 bp upstream of the transcription initiation site was cloned into a pSEAP reporter plasmid and the RTEF-1 isoforms were cloned into a pcDNA expression vector. Due to difficulties in nucleotransfection of plasmid DNA into primary cultures of ocular vascular endothelial cells, 293T cells were used as a substitute cell line for transfection studies. Co-transfection of the VEGF promoter-reporter plasmid with one of each of the RTEF-1 isoforms indicate that the 1305 bp, 936 bp and 447 bp isoforms up-regulated expression of the reporter from the VEGF promoter (lanes 1, 2, and 4 FIG. 2). However, interestingly, the 651 bp isoform down regulated expression from the VEGF promoter (lane 3, FIG. 2). The full length 1305 bp RTEF-1 product and the 936 bp isoform enhanced expression between 3-4 fold significantly higher than background (P=0.001), and no difference was observed between these 2 isoforms (P=0.01) after correcting for multiple testing. The 447 bp isoform stimulated expression about 10-15 fold (average 12×) above background expression (P=0.0003). Each co-transfection experiment was repeated in triplicate on three separate occasions with the same results.

The 651 bp isoform (lane 3, FIG. 2) significantly down-regulated expression (P=0.0026) from the VEGF promoter relative to the control (Lane 5, FIG. 2). Surprisingly, the modified version of the 651 bp isoform, the SS-651 bp-RMR product described below (Lane 6, FIG. 2) not only suppressed expression from the VEGF promoter relative to the control (P=0.0009) but was even more potent at inhibiting expression than the 651 bp isoform (P=0.0008). The 651 bp isoform (lane 3, FIG. 2) inhibited expression approximately 3-fold lower than expression observed in the control, whereas the SS-651 bp-RMR version (lane 6, FIG. 2) inhibited expression about 10-fold lower than then control (shown in lane 5, FIG. 2). The potency of the SS-651 bp-RMR is likely due to the fact that this molecule is secreted out of the cell of production combined with its ability to be imported into neighboring cells.

The ss-651-RMR bp RTEF-1 comprises the coding region for the 651 bp isoform of RTEF-1 fused at the N-terminus to the human IL-2 secretion signal sequence (SEQ ID NO:22) and fused at the C-terminus to the internalization moiety (SEQ ID NO:23). This created the "ss-651-RMR" product, which is secretable from expressing cells and importable into surrounding cells.

Example 4

Figure 3:
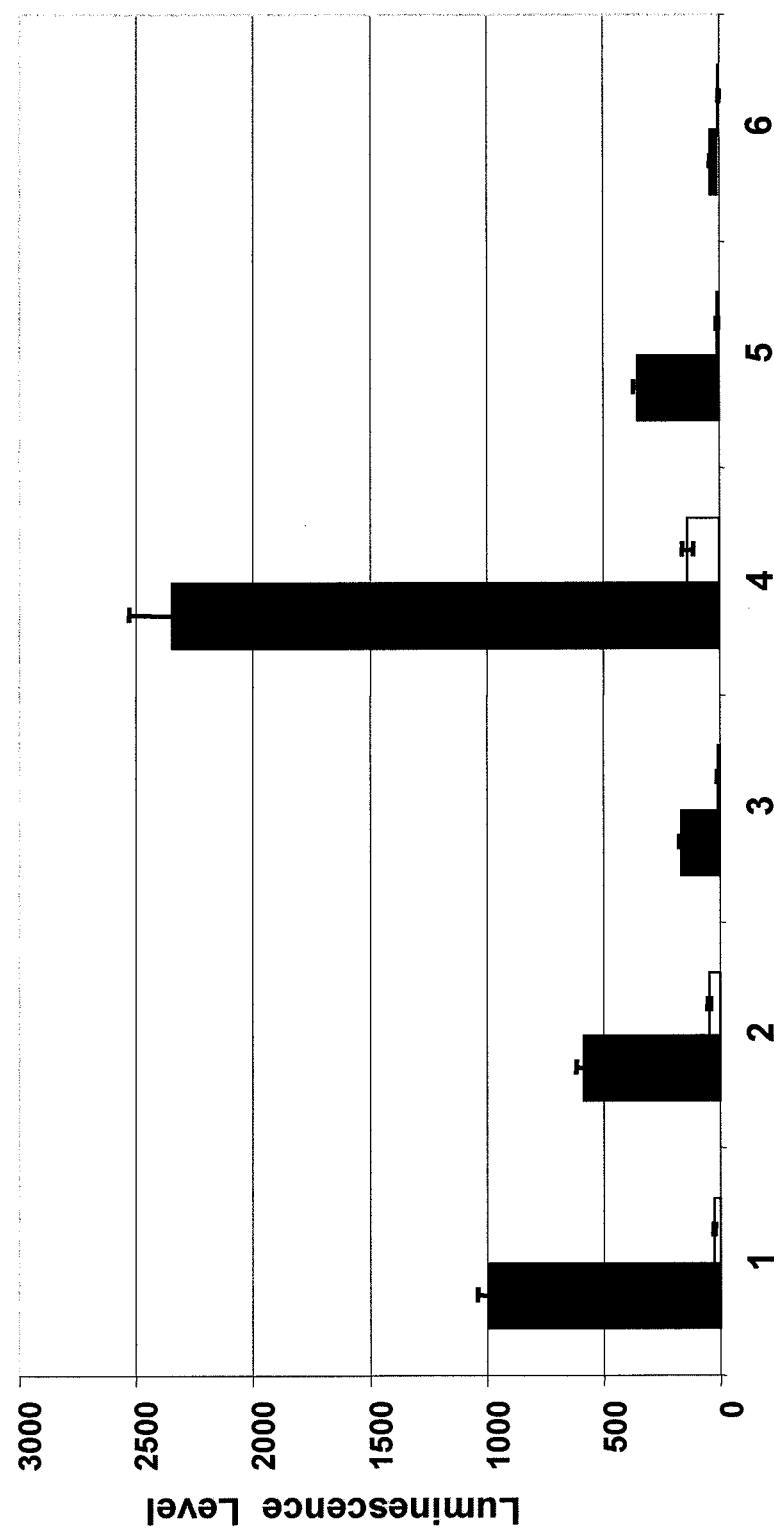
FIG. 3: RTEF-1 modulation of VEGF promoter activity is dependent on a portion of the VEGF promoter comprising 4 SP1 binding sites. Cells were transfected as described above with pcDNA expression constructs comprising the 1305 bp (lane 1), 936 bp (lane 2), 651 bp (lane 3), ss-651 bp (lane 6) or 447 bp (lane 4) RTEF-1 variants and a reporter vector comprising the intact VEGF promoter (solid boxes) or a VEGF promoter with a deletion from nucleotide −113 to −57 (open boxes). Lane five shows control VEGF promoter activity when cotransfected with an insert-less pcDNA control plasmid.

Sp1 Elements Are Required for Maximal VEGF Promoter Activity but are not Essential for RTEF Enhancer Activity Prior studies demonstrated that the full length RTEF-1 isoform binds to and requires a Sp1 element for it to augment VEGF promoter activity. In a previous study mutation of this Sp1 site situated at −97 to −89 bp resulted in loss of RTEF-1 enhancer activity (Shie et al., 2004). In the same study three other Sp1 sites within the same region −86 to −58 bp were found not to be essential for RTEF-1 enhancer activity. To test whether the new RTEF-1 isoforms required Sp1 sites for enhancer activity, the VEGF promoter with all four Sp1 sites deleted, from −113 bp to −58 bp, was cloned into a pSEAP vector and was co-transfected with each isoform. A comparison of background reporter gene expression from the full length and the Sp1-negative VEGF promoter indicates that loss of Sp1 elements results in a dramatic 30 fold decrease in reporter expression (FIG. 3). This would suggest that at least one of the four Sp1 elements within the proximal promoter is essential for enhancing overall expression. A similar level of depressed expression was noted in co-transfection experiments with the Sp1-negative and each isoform (FIG. 3, compare filled bars with open bars). However, the same trend of enhancement was still observed with the cotransfection experiments with each of the isoforms for the Sp1-negative promoter assay (FIG. 3). A 3-fold, 4-fold and 12-fold enhancement above background for the 1305 bp, 936 bp and the 447 bp isoforms, respectively. Thus, the level of enhancement above background afforded by each isoform is the same regardless of whether Sp1 elements are present within the VEGF promoter.

The 651 bp isoform remains able to inhibit expression relative to the control in the absence of the Sp1 sites within the VEGF promoter. Thus, regulation of VEGF promoter is the same for each isoform is the same regardless of whether Sp1 elements are present or not. The 651 bp fragment is capable of inhibiting the enhancer effect of the 1305 bp, 936 bp and 447 bp isoforms from the VEGF promoter in a competitive manner. That is, introducing increased amounts of 651 bp in conjunction with any of the other enhancing isoforms that normally upregulate the expression from the VEGF promoter resulted in competitive inhibition of the enhancer activity.

Example 5

Dominant Negative Transcriptional Activity of the Polypeptide from the 651 bp RTEF-1 cDNA To investigate the effects of the 651 bp isoform on the VEGF promoter enhancement of other RTEF-1 isoforms further 239T transfection experiments were undertaken. Briefly, cells were transfected with the indicated RTEF-1 enhancer expression construct (i.e., 1305 bp, 936 bp or 447 bp), a VEGF reporter vector and either an expression plasmid for the 651 bp RTEF-1 isoform or an empty vector control. Following transfection VEGF promoter activity was accessed by reporter gene assay as described previously. Results of these studies are shown in FIG. 4. In each case the enhancement activity of RTEF-1 isoforms (1305 bp, 936 bp and 447 bp) on VEGF promoter activity was repressed by co expression of the RTEF-1 651 bp isoform.

Example 6

RTEF-1 cDNA Expression Vectors Produce Expected Polypeptides in Cells

To confirm the expression of the indicated RTEF-1 polypeptides in cells 293T cells were transfected with the a control (empty vector) pcDNA expression vector or an expression vector for the 1305 bp, 936 bp, 651 bp or 447 bp cDNA sequences. Following transfection cell lysates were analyzed by Western blot using an anti-RTEF-1 antisera. Anti-RTEF-1 antisera was raised against an RTEF-1 peptide corresponding to amino acids 2-14 of the full length sequence. Antibodies for Western blot were directed to an RTEF-1 epitope that was unique relative to related human TEA proteins but shared by each of the RTEF-1 isoforms that were transfected (FIG. 5A). Results of the studies (FIG. 5B) demonstrate that each of the expected RTEF-1 polypeptides was expressed in transfected cells though in the case of the polypeptide from the 651 bp cDNA expression levels were quite low.

Example 7

In Vivo Expression of RTEF-1 in Eye Tissue

The expression of RTEF-1 isoforms in normal primate eye tissue was further studied. Western blot analysis with an anti-RTEF-1 antibody that binds to each protein isoform demonstrated RTEF-1 expression in certain tissues of the eye. Expression of RTEF-1 appeared highest in choroid and lowest in retina (FIG. 6A). Detected protein products that migrated slower than the 75 kD mass marker seem to be the full length RTEF-1 (1305 bp) isoform (FIG. 6A, upper panel). Products migrating between the 23 and 25 kD mass markers are believed to arise from the 651 bp isoform (FIG. 6A, lower panel).

In further studies that expression of RTEF-1 isoforms in the CRAO model were studied by RT-PCR. Results showed that full length (1305 bp) RTEF-1 RNA was preferentially expressed in CRAO retina relative to control retinal tissue (FIG. 6B, compare lanes 1 and 2).

To further assess the cellular distribution of RTEF-1 expression in eye tissues eye tissues were analyzed by immunohistochemistry with an RTEF-1 binding antibody. Results demonstrated the expression of RTEF-1 in the iris, ciliary body, optic nerve and retina (FIG. 7A-B).

Example 8

Localization of the RTEF-1 Isoforms

The RTEF-1 isoforms (1305 bp, 651 bp, and 447 bp) were cloned into a pMAX-FP-N vector (Amaxa Inc, Gaithersburg, Md.) with a different fluorescent protein fused to the carboxyl end of each of the isoforms respectively. The 1305 bp isoform was fused with a green fluorescent protein (GFP), while 651 bp isoform was fused with a red fluorescent protein (RFP) and the 447 bp isoform was fused with a yellow fluorescent protein (YFP). The 651 bp isoform was also cloned into a pHR-CMV-eGFP vector with a hIL-2 secretion signal and a RMR transport motif to produce a ss-651-RMR RTEF-1-GFP fusion protein. Each construct was verified by sequencing analysis. Human 293T cells were plated into 6 well plates at a density of $3 \times 10^5$ cells per well. Cells were grown to 80% confluency in DMEM media supplemented with 10% FBS and 1× concentration of penicillin-streptomycin-amphotericin. Each construct was transfected into the treated 293T cells via electroporation using the Amaxa Nucleofecter II apparatus (Amaxa Inc, Gaithersburg, Md.). Cells were incubated for 24 hours at 37° C., with 5% of $CO_2$. All transfection reactions were observed using fluorescent microscopy for fluorescent activity, and were photo-documented to record localization patterns of the RTEF-1 protein isoforms.

The fluorescent microscopy analysis demonstrates that the two VEGF-enhancer RTEF-1 isoforms (1305 bp and 447 bp) containing a nuclear localization signal were found localized to the nucleus of the cell. Furthermore, the inhibitory isoform 651 was found concentrated in the cytoplasm, outside and surrounding the nucleus. However, with a hIL-2 secretion signal sequence and a RMR transport motif, the ss-651-RMR RTEF-1 isoform was found localizing in the cell nucleus.

To confirm the localization pattern of the RTEF-1 isoforms, western immunoblot analysis was performed for the each cellular fraction with cells transfected with RTEF-1 isoforms. For these studies, cells were transfected with 2 μg of RTEF-1 isoforms and grown 24 hours. Media was then changed to serum-free DMEM and grown for an additional 48 hours. Cellular fractions were isolated and collected. Media was treated with TCA to precipitate all residual proteins in the media. RTEF-1 specific antibody, which does not distinguish among the three isoforms, was used at a concentration of 1/5000 to detect the presence of RTEF-1 protein. The nuclear fractions, cytoplasmic fractions and media were analyzed with the samples from cells transfected with a pcDNA empty vector, or a pcDNA expression vector for the 1305 bp, 936 bp, 651 bp, ss-651-RMR, or 447 bp RTEF-1 variant. The results indicated that the VEGF enhancer isoforms 1305 bp and 447 bp, increase the expression of VEGF via binding to the chromosome DNA. However, it is surprising that the 651 bp RTEF-1 negative dominant isoform localizes in the cytoplasm even though it can competitively inhibit the action of the enhancer RTEF-1 isoforms which localize in the nucleus.

Example 9

RTEF-1 Protein is Present within Human Ocular Melanoma Cells

VEGF is a key protein responsible for the development of various ocular neovascular diseases and establishment of ocular tumors. Identification of proteins that regulate the expression of the VEGF gene will help to understand the etiology and progression of ocular tumors. The most common intraocular cancer in adults is ocular melanoma (OM) and can lead to local tissue damage, loss of vision and has a tendency to metastasize which has significant consequences on patient morbidity and mortality.

The various human RTEF-1 isoforms are able to differentially potentiate expression from the VEGF 5' proximal promoter region. Since upregulation of VEGF mediates angiogenesis, inflammation and tumor progression, the inventors believe that RTEF-1 may play a role in the development and advancement of vascularized human ocular tumors such as melanoma, and possibly other non-ocular tumors. The inventors investigated whether RTEF-1 protein is present within human ocular melanoma cells by immunohistochemistry methods. A section of a human eye which had a melanoma tumor was stained with an antibody that recognizes the human RTEF-1 protein (but which does not distinguish as among the three isoforms). A slide containing the section was examined using microscopy. The results demonstrated that RTEF-1 protein (observed as red staining) is present within human ocular melanoma cell. The melanoma cells look brown, due to the presence of melanin pigment. The cells stained red and brown are tumor cells with RTEF-1 protein. The high level of RTEF-1 in those tumor cells suggests that the RTEF-1 may upregulate the VEGF gene within these cells, and promote cell proliferation and tumor expansion.

Thus, using the 651 bp RTEF-1 isoform may be used to repress VEGF expression in these melanoma cells and to inhibit the growth of this type of ocular tumor. The application of the 651 bp RTEF-1 isoform may be beneficial in the therapy of other cancers, which rely on VEGF stimulated tumor expansion.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,376,110
U.S. Pat. No. 4,554,101
U.S. Pat. No. 4,683,202
U.S. Pat. No. 4,684,611
U.S. Pat. No. 4,797,368
U.S. Pat. No. 4,816,567
U.S. Pat. No. 4,952,500
U.S. Pat. No. 5,139,941
U.S. Pat. No. 5,302,523
U.S. Pat. No. 5,322,783
U.S. Pat. No. 5,384,253,
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,136
U.S. Pat. No. 5,994,136
U.S. Pat. No. 5,994,624
U.S. Pat. No. 6,013,516
U.S. Pat. No. 7,122,181
U.S. Appln. 20030008374
U.S. Appln. 20030082789
U.S. Appln. 2004005647
U.S. Appln. 20050175591
U.S. Appln. 20060171919
U.S. Appln. 20060223114
U.S. Appln. 20060234299
U.S. patent Ser. No. 07/715,272
U.S. patent Ser. No. 07/934,373
Almendro et al., *J. Immunol.*, 157 (12):5411-5421, 1996.
Ausubel et al., In: *Current Protocols in Molecular Biology*, John, Wiley & Sons, Inc, NY, 1994.
Baichwal and Sugden, In: *Gene Transfer*, Kucherlapati (Ed.), Plenum Press, NY, 117-148, 1986.
Blomer et al., *J. Virol.*, 71 (9):6641-6649, 1997.
Brodeur et al., In: *Monoclonal antibody production techniques and applications*, Marcel Dekker, Inc., NY, 51-63, 1987.
Carbonelli et al., *FEMS Microbiol. Lett.*, 177 (1):75-82, 1999.
Chandler et al., *Proc. Natl. Acad. Sci. USA*, 94 (8):3596-601, 1997.
Chen and Okayama, *Mol. Cell. Biol.*, 7 (8):2745-2752, 1987.
Clackson et al., *Nature* 352: 624-628, 1991.
Cocea, *Biotechniques*, 23 (5):814-816, 1997.
Cotten et al., *Proc. Natl. Acad. Sci. USA*, 89 (13):6094-6098, 1992.
Coupar et al., *Gene*, 68:1-10, 1988.
Curiel, *Nat. Immun.*, 13 (2-3):141-164, 1994.
David et al., *Biochemistry*, 13:1014, 1974.
Donahue et al., *Curr. Eye Res.*, 15:175-84, 1996.
Farrance et al., *J. Biol. Chem.*, 271:8266-74, 1996.
Fechheimer, et al., *Proc Natl. Acad. Sci. USA*, 84:8463-8467, 1987.
Fraley et al., *Proc. Natl. Acad. Sci. USA*, 76:3348-3352, 1979.
Friedmann, *Science*, 244:1275-1281, 1989.
Frigerio et al., *Hum. Mol. Genet.*, 4:37-43, 1995.
Goding, In: *Monoclonal Antibodies: Principles and Practice*, 2d ed., Academic Press, Orlando, Fla., pp 60-61, 71-74, 1986.
Gopal, *Mol. Cell. Biol.*, 5:1188-1190, 1985.
Gragoudas et al., *N. Engl. J. Med.*, 351:2805-2816, 2004.
Graham and Van Der Eb, *Virology*, 52:456-467, 1973.
Griffith et al., *EMBO J.*, 12:725-734, 1993.
Grunhaus and Horwitz, *Seminar in Virology*, 3:237-252, 1992.
Harland and Weintraub, *J. Cell Biol.*, 101 (3):1094-1099, 1985.
Horwich et al. *J. Virol.*, 64:642-650, 1990.
Hunter et al., *Nature*, 144:945, 1962.
Inouye and Inouye, *Nucleic Acids Res.*, 13:3101-3109, 1985.
Jakobovits et al., *Nature*, 362:255-258, 1993.
Jakobovits et al., *Proc. Natl. Acad. Sci. USA*, 90:2551-255, 1993.
Jiang et al., *Biochemistry*, 39:3505-13, 2000.
Johnson et al., In: *Biotechnology and Pharmacy*, Pezzuto et al., eds., Chapman and Hall, New York, 1993.
Jones et al., *Nature*, 321:522-525, 1986.
Kaeppler et al., *Plant Cell Reports*, 9:415-418, 1990.
Kanda et al., *Endothelium*, 6:33-44, 1998.
Kaneda et al., *Science*, 243:375-378, 1989.
Kaneko & DePamphilis, *Dev Genet*, 22:43-55, 1998.
Kato et al, *J. Biol. Chem.*, 266:3361-3364, 1991.
Kelleher and Vos, *Biotechniques*, 17 (6):1110-7, 1994.
Kohler and Milstein, *Nature*, 256:495-497, 1975.
Kozbor, *J. Immunol.*, 133 (6):3001-3005, 1984.
Kraus et al. *FEBS Lett.*, 428 (3):165-170, 1998.
Lareyre et al., *J. Biol. Chem.*, 274 (12):8282-8290, 1999.
Lashkari et al., *Am. J. Pathol.*, 156:1337-44, 2000.
Laughlin et al., *J. Virol.*, 60 (2):515-524, 1986.
Lebkowski et al., *Mol. Cell. Biol.*, 8 (10):3988-3996, 1988.
Lee et al., *Biochem. Biophys. Res. Commun.*, 238 (2):462-467, 1997.
Levenson et al., *Hum. Gene Ther.*, 9 (8):1233-1236, 1998.
Macejak and Sarnow, *Nature*, 353:90-94, 1991.
Maniatis, et al., Molecular Cloning, A Laboratory Manual, Cold Spring Harbor Press, Cold Spring Harbor, N.Y., 1988.
Mann et al., *Cell*, 33:153-159, 1983.
Marks et al., *Bio/Technol.*, 10:779-783, 1992.
Marks et al., *J. Mol. Biol.*, 222:581-97, 1991.
McCafferty et al., *Nature*, 348:552-553, 1990.
McLaughlin et al., *J. Virol.*, 62 (6):1963-1973, 1988.
Miller et al., *Am. J. Clin. Oncol.*, 15 (3):216-221, 1992.
Miller, *Am. J. Pathol.*, 151:13-23, 1997.
Morrison et al., *Proc. Natl. Acad. Sci. USA*, 81 (21):6851-6855, 1984.
Munson and Pollard, *Anal. Biochem.*, 107:220, 1980.
Muzyczka, *Curr. Topics Microbiol. Immunol.*, 158:97-129, 1992.
Nabel et al., *Science*, 244 (4910):1342-1344, 1989.
Naldini et al., *Science*, 272 (5259):263-267, 1996.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nomoto et al., *Gene*, 236 (2):259-271, 1999.
Nygren, *J. Histochem. Cytochem.*, 30 (5):407-412, 1982.

Omirulleh et al., *Plant Mol. Biol.,* 21 (3):415-428, 1993.
Onda et al., *Cancer Res.,* 64:1419-1424, 2004.
Pain et al., *J. Immunol. Meth.,* 40:219, 1981.
Paskind et al., *Virology,* 67:242-248, 1975.
PCT Appln. WO 93/06213
PCT Appln. WO 94/09699
PCT Appln. WO 95/06128
Pe'er et al., *Lab. Invest.,* 72:638-45, 1995.
Pelletier and Sonenberg, *Nature,* 334 (6180):320-325, 1988.
Pierce et al., *Arch. Opthalmol.,* 114:1219-28, 1996.
Potrykus et al., *Mol. Gen. Genet.,* 199 (2):169-177, 1985.
Potter et al., *Proc. Natl. Acad. Sci. USA,* 81:7161-7165, 1984.
Remington's Pharmaceutical Sciences, 18th Ed. Mack Printing Company, pp. 1289-1329, 1990.
Ridgeway, In: *Vectors: A Survey of Molecular Cloning Vectors and Their Uses,* Rodriguez et al. (Eds.), Stoneham: Butterworth, 467-492, 1988.
Riechmann et al., *Nature,* 332 (6162):323-327, 1988.
Rippe, et al., *Mol. Cell. Biol.,* 10:689-695, 1990.
Rothbard et al., *Nat. Medicine,* 6 (11):1253-7, 2000.
Roux et. al., 1989
Sambrook et al., In: *Molecular cloning: a laboratory manual,* 2$^{nd}$ Ed., Cold Spring Harbor Laboratory Press, Cold Spring Harbor, N.Y., 1989.
Shie et al., *J. Biol. Chem.,* 279:25010-6, 2004.
Silverman et al., *Microvasc. Res.,* 70:32-42, 2005.
Stewart et al., *Genomics,* 37:68-76, 1996.
Temin, In: *Gene Transfer,* Kucherlapati (Ed.), NY, Plenum Press, 149-188, 1986.
Tratschin et al., *Mol. Cell. Biol.,* 4:2072-2081, 1984.
Tsumaki et al., *J. Biol. Chem.,* 273 (36):22861-22864, 1998.
Tur-Kaspa et al., *Mol. Cell. Biol.,* 6:716-718, 1986.
Vannay et al., *Pediatr. Res.,* 57:396-8, 2005.
Verhoeyen et al., *Science,* 239 (4847):1534-1536, 1988.
von Minckwitz et al., *Breast Cancer Res.,* 7:R616-626, 2005.
Waterhouse et al., *Nucl. Acids Res.,* 21:2265-2266, 1993.
Wilson et al., *Science,* 244:1344-1346, 1989.
Winthrop et al., *Clin. Cancer Res.,* 9:3845s-3853s, 2003.
Wong et al., *Gene,* 10:87-94, 1980.
Wright et al., *Curr. Protein Pept. Sci.,* 4 (2):105-24, 2003.
Wu and Wu, *Biochemistry,* 27: 887-892, 1988.
Wu and Wu, *J. Biol. Chem.,* 262:4429-4432, 1987.
Wu et al., *Biochem. Biophys. Res. Commun.,* 233 (1):221-226, 1997.
Yasunami et. al., *Biochem. Biophys. Res. Commun.,* 228:365-70, 1996.
Yockey et al., *J. Biol. Chem.,* 271:3727-36, 1996.
Young et al., *J. Aapos.* 1:105-10, 1997.
Zhao-Emonet et al., *Biochim. Biophys. Acta,* 1442 (2-3):109-119, 1998.
Zola, In: *Monoclonal Antibodies: A Manual of Techniques,* CRC Press, Inc., 147-158, 1987.
Zufferey et al., *Nat. Biotechnol.,* 15 (9):871-875, 1997.
Zuzarte et al., *Biochim. Biophys. Acta.,* 1517:82-90, 2000.

What is claimed is:

1. An isolated polypeptide that is at least 95% identical to SEQ ID NO:2; SEQ ID NO:3 or SEQ ID NO:4.

2. The isolated polypeptide of claim 1, wherein the polypeptide consists of SEQ ID NO: 3.

3. The isolated polypeptide of claim 1, wherein the amino acid sequence is at least 95% identical to SEQ ID NO:2.

4. The isolated polypeptide of claim 3, wherein the amino acid sequence is at least 98% identical to SEQ ID NO:2.

5. The isolated polypeptide of claim 4, wherein the amino acid sequence is identical to SEQ ID NO:2.

6. The isolated polypeptide of claim 1, wherein the amino acid sequence is at least 95% identical to SEQ ID NO:3.

7. The isolated polypeptide of claim 6, wherein the amino acid sequence is at least 98% identical to SEQ ID NO:3.

8. The isolated polypeptide of claim 7, wherein the amino acid sequence is identical to SEQ ID NO:3.

9. The isolated polypeptide of claim 1, wherein the amino acid sequence is at least 95% identical to SEQ ID NO:4.

10. The isolated polypeptide of claim 9, wherein the amino acid sequence is at least 98% identical to SEQ ID NO:4.

11. The isolated polypeptide of claim 10, wherein the amino acid sequence is identical to SEQ ID NO:4.

12. The isolated polypeptide of claim 1, further comprising a secretion signal sequence.

13. The isolated polypeptide of claim 1, further comprising a cell internalization moiety.

14. The isolated polypeptide of claim 13, wherein the internalization moiety is a peptide, a polypeptide, an aptamer or an avimer.

15. The isolated polypeptide of claim 14, wherein the internalization moiety comprises internalization sequences from HIV tat, HSV-1 tegument protein VP22, or Drosophila antennopedia.

16. The isolated polypeptide of claim 14, wherein the internalization moiety comprises a poly-arginine, a poly-methionine and/or a poly-glycine peptide.

17. The isolated polypeptide of claim 13, wherein the internalization moiety comprises the amino acid sequence RMRRMRRMRR (SEQ ID NO:23).

18. The isolated polypeptide of claim 13, wherein the internalization moiety is an antibody.

19. The isolated polypeptide of claim 18, wherein the antibody is an IgA, an IgM, an IgE, an IgG, a Fab, a F(ab')2, a single chain antibody, or a paratope peptide.

20. The isolated polypeptide of claim 13, further comprising a cell secretion signal.

21. The isolated polypeptide of claim 20, wherein the cell secretion signal comprises a human IL-2 secretion signal sequence (SEQ ID NO:22).

22. The isolated polypeptide of claim 21, further defined as comprising the amino acid sequence of SEQ ID NO:3, SEQ ID NO:22 and SEQ ID NO:23.

23. A method for treating a patient with an angiogenic disorder comprising administering to the patient an effective amount of a therapeutic composition comprising the polypeptide according to claim 6.

24. The method of claim 23, wherein the angiogenic disorder is ocular neovascularization, an arterio-venous malformation, coronary restenosis, peripheral vessel restenosis, glomerulonephritis, or rheumatoid arthritis.

25. The method of claim 24, wherein the angiogenic disorder is ocular neovascularization.

26. The method of claim 23, wherein the ocular neovascularization is due to macular degeneration, corneal graft rejection, retinopathy of prematurity (ROP), or diabetic retinopathy.

27. The method of claim 26, wherein the ocular neovascularization is due to age-related macular degeneration (AMD).

28. The method of claim 23, further comprising administering a second anti-angiogenic therapy.

29. The method of claim 28, wherein the second anti-angiogenic therapy is an antibody that binds to VEGF, a VEGF receptor, FGF, or an FGF receptor.

30. The method of claim 28, wherein the second anti-angiogenic therapy is bevacizumab, ranibizumab, or pegaptanib sodium.

31. The method of claim 23, wherein the angiogenic disorder is a cancer.

32. The method of claim 31, wherein the cancer is a metastatic cancer.

33. The method of claim 31, wherein the cancer is a bladder, blood, bone, bone marrow, brain, breast, colon, esophagus, eye, gastrointestinal, gum, head, kidney, liver, lung, nasopharynx, neck, ovary, prostate, skin, stomach, testis, tongue, or uterus cancer.

34. The method of claim 33, wherein the cancer is an eye cancer that is further defined as ocular melanoma.

35. The method of claim 31, further comprising administering a second anticancer therapy.

36. The method of claim 35, wherein the second anticancer therapy is chemotherapy, surgical therapy, immunotherapy, or radiation therapy.

37. The method of claim 23, wherein the patient is a human.

38. The method of claim 23, wherein the therapeutic composition is administered systemically.

39. The method of claim 23, wherein the therapeutic composition is administered locally.

40. The method of claim 23, wherein the therapeutic composition is administered to the eye.

41. The method of claim 40, wherein the therapeutic composition is administered topically to the eye or by intraocular injection.

42. The method of claim 41, wherein the therapeutic composition is administered topically to the eye as an eye drop.

* * * * *